(12) United States Patent
Drmanac

(10) Patent No.: US 10,125,392 B2
(45) Date of Patent: **\*Nov. 13, 2018**

(54) PREPARING A DNA FRAGMENT LIBRARY FOR SEQUENCING USING TAGGED PRIMERS

(71) Applicant: Complete Genomics, Inc., Mountain View, CA (US)

(72) Inventor: Radoje Drmanac, Los Altos Hills, CA (US)

(73) Assignee: Complete Genomics, Inc., San Jose, CA (US)

( * ) Notice: Subject to any disclaimer, the term of this patent is extended or adjusted under 35 U.S.C. 154(b) by 551 days.

This patent is subject to a terminal disclaimer.

(21) Appl. No.: 13/971,797

(22) Filed: Aug. 20, 2013

(65) Prior Publication Data

US 2013/0345068 A1 Dec. 26, 2013

Related U.S. Application Data

(60) Division of application No. 13/954,778, filed on Jul. 30, 2013, now Pat. No. 8,673,562, and a division of
(Continued)

(51) Int. Cl.
*C12Q 1/68* (2006.01)
*C12Q 1/6874* (2018.01)
(Continued)

(52) U.S. Cl.
CPC .......... *C12Q 1/6874* (2013.01); *C07H 21/04* (2013.01); *C07K 1/047* (2013.01); *C12Q 1/682* (2013.01);
(Continued)

(58) Field of Classification Search
None
See application file for complete search history.

(56) References Cited

U.S. PATENT DOCUMENTS 4,719,179 A    1/1988 Baranay .................. 432/172.1
4,883,750 A   11/1989 Whiteley ...................... 435/6
(Continued)

FOREIGN PATENT DOCUMENTS

JP    4-262799    9/1992
JP    4-304900    10/1992
(Continued)

OTHER PUBLICATIONS

Hosono et al. Unbiased whole-genome amplification directly from clinical samples. Genome Research 13:954-964 (2003).*
(Continued)

*Primary Examiner* — Samuel C Woolwine
(74) *Attorney, Agent, or Firm* — Kilpatrick Townsend & Stockton LLP

(57) ABSTRACT

The invention provides methods and kits for ordering sequence information derived from one or more target polynucleotides. In one aspect, one or more tiers or levels of fragmentation and aliquoting are generated, after which sequence information is obtained from fragments in a final level or tier. Each fragment in such final tier is from a particular aliquot, which, in turn, is from a particular aliquot of a prior tier, and so on. For every fragment of an aliquot in the final tier, the aliquots from which it was derived at every prior tier is known, or can be discerned. Thus, identical sequences from overlapping fragments from different aliquots can be distinguished and grouped as being derived from the same or different fragments from prior tiers. When the fragments in the final tier are sequenced, overlapping sequence regions of fragments in different aliquots are used to register the fragments so that non-overlapping regions are ordered. In one aspect, this process is carried out in a hierarchical fashion until the one or more target polynucleotides are characterized, e.g. by their nucleic
(Continued)

acid sequences, or by an ordering of sequence segments, or by an ordering of single nucleotide polymorphisms (SNPs), or the like.

18 Claims, 8 Drawing Sheets

Specification includes a Sequence Listing.

Related U.S. Application Data application No. 13/017,244, filed on Jan. 31, 2011, now Pat. No. 8,765,379, said application No. 13/954,778 is a division of application No. 13/017,244, filed on Jan. 31, 2011, now Pat. No. 8,765,379, which is a continuation of application No. 12/335,168, filed on Dec. 15, 2008, now Pat. No. 7,901,891, which is a continuation of application No. 11/451,692, filed on Jun. 13, 2006, now Pat. No. 7,709,197.

(60) Provisional application No. 60/776,415, filed on Feb. 24, 2006, provisional application No. 60/725,116, filed on Oct. 7, 2005, provisional application No. 60/690,771, filed on Jun. 15, 2005.

(51) Int. Cl.
| | |
|---|---|
| C12Q 1/682 | (2018.01) |
| C12Q 1/6837 | (2018.01) |
| C12Q 1/6869 | (2018.01) |
| C07H 21/04 | (2006.01) |
| C07K 1/04 | (2006.01) |
| G01N 15/14 | (2006.01) |
| C12Q 1/6806 | (2018.01) |

(52) U.S. Cl.
CPC ......... *C12Q 1/6806* (2013.01); *C12Q 1/6837* (2013.01); *C12Q 1/6869* (2013.01); *G01N 15/1404* (2013.01); *G01N 15/1434* (2013.01); *C12Q 2525/151* (2013.01); *C12Q 2525/313* (2013.01); *C12Q 2531/125* (2013.01); *C12Q 2565/513* (2013.01); *Y10S 977/778* (2013.01); *Y10S 977/789* (2013.01); *Y10S 977/792* (2013.01); *Y10S 977/88* (2013.01); *Y10S 977/882* (2013.01)

(56) References Cited

U.S. PATENT DOCUMENTS

| | | | |
|---|---|---|---|
| 5,091,302 A | 2/1992 | Newman | 435/6 |
| 5,124,246 A | 6/1992 | Urdea | 435/6 |
| 5,143,854 A | 9/1992 | Pirrung | 436/518 |
| 5,202,231 A | 4/1993 | Drmanac | 435/6 |
| 5,354,668 A | 10/1994 | Auerbach | 435/91.1 |
| 5,403,708 A | 4/1995 | Brennan et al. | |
| 5,426,180 A | 6/1995 | Kool | 536/25.3 |
| 5,427,930 A | 6/1995 | Birkenmeyer | 435/91.52 |
| 5,474,796 A | 12/1995 | Brennan | 427/2.13 |
| 5,492,806 A | 2/1996 | Drmanac et al. | |
| 5,508,169 A | 4/1996 | Deugau | 435/6 |
| 5,525,464 A | 6/1996 | Drmanac | 435/6 |
| 5,632,957 A | 5/1997 | Heller et al. | |
| 5,641,658 A | 6/1997 | Adams | 435/91.2 |
| 5,648,245 A | 7/1997 | Fire | 435/91.1 |
| 5,710,000 A | 1/1998 | Sapolsky et al. | |
| 5,714,320 A | 2/1998 | Kool | 435/6 |
| 5,728,524 A | 3/1998 | Sibson | 435/6 |
| 5,744,305 A | 4/1998 | Fodor | 435/6 |
| 5,800,992 A | 9/1998 | Fodor | 435/6 |
| 5,854,033 A | 12/1998 | Lizardi | 435/91.2 |
| 5,866,337 A | 2/1999 | Schon | 435/6 |
| 5,871,921 A | 2/1999 | Landegren | 435/66 |
| 5,888,737 A | 3/1999 | DuBridge | 435/6 |
| 5,994,068 A | 11/1999 | Guilfoyle | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,054,100 A * | 4/2000 | Stanchfield | B01J 19/0046 422/534 |
| 6,077,668 A | 6/2000 | Kool | 435/6 |
| 6,096,880 A | 8/2000 | Kool | 536/25.3 |
| 6,124,120 A | 9/2000 | Lizardi | 435/91.2 |
| 6,136,537 A | 10/2000 | Macevicz | 435/6 |
| 6,143,495 A | 11/2000 | Lizardi | 435/6 |
| 6,143,527 A | 11/2000 | Pachuk | 435/91.1 |
| 6,210,891 B1 | 4/2001 | Nyren | 435/6 |
| 6,210,894 B1 | 4/2001 | Brennan | 435/6 |
| 6,218,152 B1 | 4/2001 | Auerbach | 435/91.2 |
| 6,221,603 B1 | 4/2001 | Mahtani | 435/6 |
| 6,255,469 B1 | 7/2001 | Seeman | 536/23.1 |
| 6,258,539 B1 | 7/2001 | Hunkapillar | 435/6 |
| 6,261,808 B1 | 7/2001 | Auerbach | 435/91.1 |
| 6,270,961 B1 | 8/2001 | Drmanac | 435/6 |
| 6,274,320 B1 | 8/2001 | Rothberg | 435/6 |
| 6,274,351 B1 | 8/2001 | Peponnet | 435/91.1 |
| 6,284,497 B1 | 9/2001 | Sabanayagam | 435/91.2 |
| 6,287,824 B1 | 9/2001 | Lizardi | 435/91.2 |
| 6,291,183 B1 | 9/2001 | Pirrung | 435/6 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |
| 6,329,150 B1 | 12/2001 | Lizardi | 435/6 |
| 6,344,329 B1 | 2/2002 | Lizardi | 435/6 |
| 6,346,413 B1 | 2/2002 | Fodor | 435/287.2 |
| 6,355,419 B1 | 3/2002 | Alfenito | 435/6 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,432,360 B1 | 8/2002 | Church | 422/68.1 |
| 6,472,156 B1 | 10/2002 | Wittwer | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Baranay | 435/91.2 |
| 6,558,928 B1 | 5/2003 | Landegren | 435/91.1 |
| 6,573,369 B2 | 6/2003 | Henderson | 536/23.1 |
| 6,576,448 B2 | 6/2003 | Weissman | 435/91.2 |
| 6,589,726 B1 | 7/2003 | Butler | 435/4 |
| 6,610,481 B2 | 8/2003 | Koch | 435/6 |
| 6,610,491 B2 | 8/2003 | Mirkin et al. | |
| 6,620,584 B1 | 9/2003 | Chee | 435/6 |
| 6,632,609 B2 | 10/2003 | Lizardi | 435/6 |
| 6,632,641 B1 * | 10/2003 | Brennan | C12Q 1/6837 435/287.2 |
| 6,653,077 B1 | 11/2003 | Brenner | 435/6 |
| 6,660,229 B2 | 12/2003 | Cantor et al. | |
| 6,783,943 B2 | 8/2004 | Christian | 435/6 |
| 6,787,308 B2 | 9/2004 | Balasubramanian | 435/6 |
| 6,812,005 B2 | 11/2004 | Fan | 435/91.2 |
| 6,828,100 B1 | 12/2004 | Ronaghi | |
| 6,833,246 B2 | 12/2004 | Balasubramanian | |
| 6,864,052 B1 | 3/2005 | Drmanac | 435/6 |
| 6,890,741 B2 | 5/2005 | Fan | 435/91.2 |
| 6,913,884 B2 | 7/2005 | Stuelpnagel | 435/6 |
| 6,975,943 B2 | 12/2005 | Gibbs | 702/20 |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,074,600 B2 | 7/2006 | Dean et al. | |
| 7,083,929 B2 | 8/2006 | Wong | 435/6 |
| 7,232,656 B2 | 6/2007 | Balasubramanian | 435/6 |
| 7,244,559 B2 | 7/2007 | Rothberg | 435/6 |
| 7,264,929 B2 | 9/2007 | Rothberg | 435/6 |
| 7,276,720 B2 | 10/2007 | Ulmer | 356/246 |
| 7,297,778 B2 | 11/2007 | Matsuzaki | 536/22.1 |
| 7,384,737 B2 | 6/2008 | Barnes | 435/6 |

(56) References Cited

U.S. PATENT DOCUMENTS

| | | | |
|---|---|---|---|
| 7,544,473 B2 | 6/2009 | Brennar | 435/6 |
| 7,565,346 B2 | 7/2009 | Fan et al. | |
| 7,709,197 B2 | 5/2010 | Drmanac | |
| 7,807,375 B2 | 10/2010 | Cantor et al. | |
| 7,897,344 B2 | 3/2011 | Dahl et al. | |
| 7,901,891 B2 | 3/2011 | Drmanac | |
| 8,592,150 B2 | 11/2013 | Drmanac et al. | |
| 8,673,562 B2 | 3/2014 | Drmanac et al. | |
| 8,765,375 B2 | 7/2014 | Drmanac et al. | |
| 8,765,379 B2 | 7/2014 | Drmanac et al. | |
| 8,765,382 B2 | 7/2014 | Drmanac et al. | |
| 8,771,957 B2 | 7/2014 | Drmanac et al. | |
| 8,771,958 B2 | 7/2014 | Drmanac et al. | |
| 2002/0004204 A1 | 1/2002 | O'Keefe | 435/6 |
| 2002/0012930 A1 | 1/2002 | Rothberg | 435/6 |
| 2002/0012939 A1 | 1/2002 | Palsson | |
| 2002/0019007 A1* | 2/2002 | Jensen | C12Q 1/689 435/6.12 |
| 2002/0025532 A1 | 2/2002 | Huang et al. | |
| 2002/0055100 A1 | 5/2002 | Kawashima | 435/6 |
| 2002/0065609 A1 | 5/2002 | Ashby | |
| 2002/0076716 A1 | 6/2002 | Sabanayagam | 435/6 |
| 2002/0094536 A1* | 7/2002 | Lofquist | C12N 15/10 435/6.11 |
| 2002/0197621 A1 | 12/2002 | Drmanac | 435/6 |
| 2003/0068629 A1 | 4/2003 | Rothberg | 435/6 |
| 2003/0092007 A1 | 5/2003 | Gibbs | 702/20 |
| 2003/0100006 A1 | 5/2003 | Senapathy | |
| 2003/0148313 A1 | 8/2003 | Strathmann | |
| 2004/0002090 A1 | 1/2004 | Mayer | 435/6 |
| 2004/0029165 A1 | 2/2004 | Wong | |
| 2004/0229221 A1 | 11/2004 | Schon | 435/6 |
| 2004/0248144 A1 | 12/2004 | Mir | 435/6 |
| 2004/0248161 A1 | 12/2004 | Rothberg | 435/6 |
| 2004/0259118 A1 | 12/2004 | Macevicz | 435/6 |
| 2005/0019776 A1 | 1/2005 | Callow | 435/6 |
| 2005/0037356 A1 | 2/2005 | Gullberg | 435/6 |
| 2005/0042633 A1 | 2/2005 | Williams | |
| 2005/0042649 A1 | 2/2005 | Balasubramanian | 435/6 |
| 2005/0100939 A1 | 5/2005 | Namsaraev | 435/6 |
| 2005/0130173 A1 | 6/2005 | Leamon et al. | |
| 2005/0191656 A1 | 9/2005 | Drmanac | 435/6 |
| 2005/0202489 A1 | 9/2005 | Choi et al. | |
| 2005/0214840 A1 | 9/2005 | Chen | 435/6 |
| 2005/0244863 A1 | 11/2005 | Mir | 435/6 |
| 2006/0012793 A1 | 1/2006 | Harris | |
| 2006/0024681 A1 | 2/2006 | Smith | 435/6 |
| 2006/0024711 A1 | 2/2006 | Lapidus | 435/6 |
| 2006/0073506 A1 | 4/2006 | Christians et al. | |
| 2006/0110764 A1 | 5/2006 | Tang et al. | |
| 2006/0223097 A1 | 10/2006 | Sapolosky | 435/6 |
| 2006/0263789 A1* | 11/2006 | Kincaid | C12Q 1/68 435/6.12 |
| 2007/0015182 A1 | 1/2007 | Abarzua | 435/6 |
| 2007/0037152 A1 | 2/2007 | Drmanac | |
| 2007/0037197 A1 | 2/2007 | Young et al. | |
| 2007/0042401 A1 | 2/2007 | Morgan et al. | |
| 2007/0054311 A1 | 3/2007 | Kamberov et al. | |
| 2007/0072208 A1 | 3/2007 | Drmanac | |
| 2007/0099208 A1 | 5/2007 | Drmanac et al. | |
| 2008/0051294 A1 | 2/2008 | Gormley et al. | |
| 2008/0234136 A1 | 9/2008 | Drmanac et al. | |
| 2008/0318796 A1 | 12/2008 | Drmanac | 506/3 |
| 2009/0005252 A1 | 1/2009 | Drmanac et al. | |
| 2009/0005259 A1 | 1/2009 | Drmanac et al. | |
| 2009/0011416 A1 | 1/2009 | Drmanac et al. | |
| 2009/0011943 A1 | 1/2009 | Drmanac et al. | |
| 2009/0036316 A1 | 2/2009 | Drmanac | |
| 2009/0099041 A1 | 4/2009 | Church et al. | |
| 2009/0118488 A1 | 5/2009 | Drmanac et al. | |
| 2009/0137404 A1 | 5/2009 | Drmanac et al. | |
| 2009/0137414 A1 | 5/2009 | Drmanac | 506/9 |
| 2009/0155781 A1 | 6/2009 | Drmanac et al. | |
| 2009/0264299 A1 | 10/2009 | Drmanac | 506/3 |
| 2010/0199155 A1 | 8/2010 | Kermani et al. | |
| 2011/0033854 A1 | 2/2011 | Drmanac et al. | |
| 2011/0059865 A1* | 3/2011 | Smith | B01J 19/0046 506/16 |
| 2011/0319281 A1 | 12/2011 | Drmanac | |
| 2013/0059740 A1 | 3/2013 | Drmanac et al. | |
| 2013/0124100 A1 | 5/2013 | Drmanac et al. | |

FOREIGN PATENT DOCUMENTS

| | | | |
|---|---|---|---|
| WO | WO 95/09248 | 4/1995 | |
| WO | 01/09384 A2 | 2/2001 | |
| WO | WO 01/62982 | 8/2001 | |
| WO | 02/061143 A2 | 8/2002 | |
| WO | WO 02/061143 A2 * | 8/2002 | C12Q 1/6809 |
| WO | WO 02/074988 | 9/2002 | |
| WO | 02/103046 A1 | 12/2002 | |
| WO | WO 02/103046 | 12/2002 | |
| WO | WO 03/012119 | 2/2003 | |
| WO | 03/040391 A2 | 5/2003 | |
| WO | 03/102231 A1 | 12/2003 | |
| WO | WO 2004/072294 | 8/2004 | |
| WO | WO 2004/076683 | 9/2004 | |
| WO | 2005003375 A2 | 1/2005 | |
| WO | WO 2005/040425 | 5/2005 | |
| WO | WO 2005/047523 | 5/2005 | |
| WO | WO 2005/078130 | 8/2005 | |
| WO | WO 2005/080605 | 9/2005 | |
| WO | WO 2005/082098 | 9/2005 | |
| WO | WO 2005/093094 | 10/2005 | |
| WO | WO 2005/116262 | 12/2005 | |
| WO | WO 2006/007207 | 1/2006 | |
| WO | WO 2006/040549 | 4/2006 | |
| WO | WO 2006/055521 | 5/2006 | |
| WO | WO 2006/073504 | 7/2006 | |
| WO | WO 2006/084132 | 8/2006 | |
| WO | 2006/138257 A2 | 12/2006 | |
| WO | WO 2007/014397 | 2/2007 | |
| WO | WO 2007/025124 | 3/2007 | |
| WO | 2007/037678 A2 | 4/2007 | |
| WO | 2007/044245 A2 | 4/2007 | |
| WO | WO 2007/061425 | 5/2007 | |
| WO | WO 2007/062160 | 5/2007 | |
| WO | 2007/106509 A2 | 9/2007 | |
| WO | 2007/120208 A2 | 10/2007 | |
| WO | 2007/121489 A2 | 10/2007 | |
| WO | 2007/133710 A2 | 11/2007 | |

OTHER PUBLICATIONS

Illumine Genome Network, Data Sheet: Genome Network Services "Phasing Analysis Service for Whole Human Genome Sequencing" downloaded on Jul. 19, 2013 from www.illumina.com.. 4 pages.

Brenner et al., "Gene Expression Analysis by Massivly parallel Signature Sequencing (MPSS) on Microbead Arrays" Nature Biotechnology, v. 18, pp. 630-634 (2000).

Hubbell E. "Multiplex Sequencing by Hybridization" Journal of Computational Biology, Mary Anne Liebert Inc., US vol. 8, No. 2, (2001) pp. 141-149.

Jiang et al., "Old can be new again: HAPPY whole genome sequencing, mapping and assembly" Int. J. Biol. Sci. 2009, 5 pp. 298-303.

Cheung et al (1996) Whole genome amplification using a degenerate oligonucleotide primer allows hundreds of genotypes to be performed on less than one nanogram of genomic DNA. Proc. Natl. Acad. Sci. USA 93:14676-14679.

Drmanac, et al., "Human Genome Sequencing Using Unchained Base Reads on Self-Assembling DNA Nanoarrays," Science, Jan. 2010, vol. 327, No. 78, pp. 78-81.

Delius et al, "Separation of complementary strands of plasmid DNA using the biotin-avidin system and its application to heteroduplex formation and RNA/DNA hybridizations in electron microscopy," Nucleic Acids Research, 13: 5457-5469 (1985).

Drmanac et al., "Sequencing by Hybridization (SBH): Advantages, Achievements, and Opportunities", Adv. Biochem. Engineering/Biotechnology, 2002, 77: 76-101.

(56) References Cited

OTHER PUBLICATIONS

Henke et al., "Betaine Improves the PCR Aplification of GC-Rich DNA Sequences", Nucleic Acids Research, 1997, 25(19);3957-3958.
Kandpal et al., "Selective Enrichment of a Large Size Genomic DNA Fragment by Affinity Capture: An Approach for Genome Mapping", Nucleic Acids Research, 1990, 18:1789.
Kelly et al., "Miniaturizing Chemistry and Biology in Microdroplets", Chemical Communications, 2007, 18:1773-1788.
Li et al., "BEAMing up for Detection and Quantification of Rare Sequence Variants", Nature Methods, 2006, 3:95-97.
Metzker, "Emerging Technologies in DNA Sequencing", Genome Research, 2005, 15:1767-1776.
Prodromou et al., "DNA Fragmentation-Based Combinatorial Approached to Soluble Protein Expression. Part 1. Generating DNA fragment libraries.", Drug Discovery Today, 2007, 12(12-22):931-938.
Ramsay et al., "Intimate Association of Microsatellite Repeats with Retrotransposons and other Dispersed Repetitive Elements in Barley", The Plant Journal, 1999, 17(4):415-425.
Reich et al., "Combinatorial Domain Hunting: An Effective Approach for the Identification of Soluble Protein Domains Adaptable to High-Throughput Applications", Protein Science, 2006, 15(10):2357.
Williams et al., "Amplification of Complex Gene Libraries by Emulsion PCR", Nature Methods, 2006, 3(7):545-550.
Search Report for EP Application No. 06760745.7, mailed on Sep. 17, 2009, 11 pages.
International Search Report and Written Opinion for PCT/US2010/038741, mailed on May 27, 2011, 23 pages.
Batzoglou et al, "ARACHNE: A whole-genome shotgun assembler," Genome Research, 12: 177-189 (2002).
Blanco et al., "Highly efficient DNA synthesis by the phage phi 29 DNA polymerase," J. Biol. Chem., v. 264, issue 15, p. 8935-8940 (1989).
Burgtorf, C., et al., "Clone-based systematic haplotyping (CSH): a Procedure for Physical Haplotyping of Whole Genomes," Genome Research, vol. 13, No. 12, (Dec. 2003).
Callow, Matthew J., et al. "Selective DNA amplification from complex genomes using universal double-sided adapters," Nucleic Acids Research, vol. 32, No. 2, e21, p. 1-6, (Jan. 2004).
Chen et al., "A Homogeneous, Ligase-Mediated DNA Diagnostic Test", Genome Research, vol. 8, No. 5, May 1998, pp. 549-556.
Collins et al, "Directional cloning of DNA fragments at a large distance from an initial probe: A circularization method," Proc. Natl. Acad. Sci., 81: 6812-6816 (1984).
Cowie et al, "Identification of APC gene mutations in colorectal cancer using universal microarray-based combinatorial sequencing-by-hybridization," Human Mutation, 24:261-271 (2004).
Cui et al, "Determination of gene organization in individual haplotypes by analyzing single DNA fragments from single spermatozoa," Proc. Natl. Acad. Sci., 95: 10791-10796 (1998).
Dahl et al, "Multiplex amplification enabled by selective circularization of large sets of genomic DNA fragments," Nucleic Acids Research, 33(8): e71 (2005).
Dear et al, "Happy mapping: linkage mapping using a physical analogue of meiosis," Nucleic Acids Research, 21: 13-20 (1993).
Dear et al, "A high-resolution metric HAPPY map of human chromosome 14," Genomics, 48, 232-241 (1998).
Havlak et al, "The Atlas genome assembly system," Genome Research, 14: 721-732 (2004).
Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).
Lander and Waterman, "Genomic mapping by fingerprinting random clones: A mathematical analysis," Genomics, 2: 231-239 (1988).
Li et al, "Estimating the repeat structure and length of DNA sequences using I-tuples," Genome Research, 13: 1916-1922 (2003).

Mitra et al, "Digital genotyping and haplotyping with polymerase colonies," Proc. Natl. Acad. Sci., 100: 5926-5931 (2003).
Paul, P., et al., "Single-Molecule Dilution and Multiple Displacement Amplification for Molecular Haplotyping," Biotechniques, v. 38, No. 4, p. 553-559 (Apr. 4, 2005).
Pevzner et al, "An Eulerian path approach to DNA fragment assembly," Proc. Natl. Acad. Sci., 98: 9748-9753 (2001).
Shendure et al, "Accurate multiplex polony sequencing of an evolved bacterial genome," Science, 309: 1728-1732 (2005).
Shendure et al, "Advanced Sequencing Technologies: Methods and Goals," Nature Reviews Genetics, vol. 5, pp. 335-344 (2004).
Smirnov et al, "Method of manufacturing whole-genome microarrays by rolling circle amplification," Genes, Chromosomes & Cancer, 40: 72-77 (2004).
Tringe et al, "Metagenomics: DNA Sequencing of Environmental Samples," Nature Reviews Genetics, vol. 6, pp. 805-814 (2005).
Vingron et al., "Sequence Alignment and Penalty Choice Review of Concepts, Case Studies and Implications," J. Mol. Biol, vol. 235, Issue 1, pp. 1-12 (1994).
Vogelstein and Kinzer, "Digital PCR," Proc. Nati. Acad. Sci., 96: 9236-9241 (1999).
Voss, H. et al., "Efficient Low Redundancy Large-Scale DNA Sequencing at EMBL," J. of Biotechn., v. 41, No. 2, (1995).
Waterston et al, "On the sequencing of the human genome," Proc. Natl. Acad. Sci., 99: 3712-3716 (2002).
Documents on file in U.S. Appl. No. 11/451,692 (now issued as U.S. Pat. No. 7,910,354): Non-Final Office Action (Jun. 5, 2008); Response (Dec. 5, 2008); Ex Parte Quayle Action Apr. 17, 2009); Response (Jun. 17, 2009).
Documents on file in U.S. Appl. No. 12/335,168 (now issued as U.S. Pat. No. 7,901,891): Non-Final Office Action (Nov. 19, 2009); Supplemental Non-Final Office Action (Dec. 1, 2009); Response (Mar. 31, 2010); Final Office Action (Aug. 11, 2010); Response (Oct. 11, 2010).
Documents on file in U.S. Appl. No. 13/017,244: Non-Final Office Action (Aug. 1, 2012); Response Feb. 1, 2013); Supplemental Response (Feb. 4, 2013); Interview Summary (Feb. 25, 2013); Supplemental Response (Apr. 4, 2013); Interview Summary (Jul. 22, 2013); Final Office Action (Oct. 2, 2013).
Documents on file in Canadian Application No. 2,611,743: Office Action (Oct. 16, 2012); Response (Apr. 16, 2013).
Documents on file in European Application No. 06760745.7: European Search Report and Search Opinion (Sep. 17, 2009); Office Action (Jan. 11, 2010); Response (Jan. 13, 2010); Office Action (Sep. 2, 2010); Response (Mar. 14, 2011); Office Action (Jul. 18, 2012); Response (May 15, 2013); Office Action (Jul. 15, 2013).
Documents on file in European Application No. 12150825.3: European Search Report and Search Opinion (Jul. 17, 2012); Office Action (Jun. 27, 2013).
Documents on file in International Application No. PCT/US2006/022950: International Search Report (Dec. 13, 2007); International Preliminary Report on Patentability (Dec. 17, 2007).
Documents on file in U.S. Appl. No. 12/816,365: Non-Final Office Action (Mar. 29, 2012); Response (Oct. 1, 2012); Final Office Action (Jan. 4, 2013); Interview Summary (Jun. 3, 2013); Notice of Appeal (Jun. 4, 2013); Response (Jul. 10, 2013).
Documents on file in Chinese Application No. 201080036235.6: Office Action (Nov. 5, 2012); Response (May 20, 2013); Office Action (Sep. 16, 2013).
Documents on file in European Application No. 10725582.0: Office Action (Dec. 10, 2012); Response (Jun. 20, 2013); Office Action (Jul. 3, 2013); Response (Sep. 16, 2013).
Documents on file in International Application No. PCT/US2010/038741: International Search Report (Jul. 21, 2011); International Preliminary Report on Patentability (Dec. 16, 2011).
Documents on file in U.S. Appl. No. 13/448,279: Non-Final Office Action (Mar. 28, 2013); Interview Summary (Aug. 21, 2013); Interview Summary (Aug. 23, 2013); Response (Aug. 27, 2013); Interview Summary (Aug. 28, 2013); Supplemental Response (Sep. 23, 2013).
Wolfe et al., "A Genotyping Strategy Based on Incorporation and Cleavage of Chemically Modified Nucleotides," Proceedings of the National Academy of Sciences, 99(17):11073-11078 (2002).

(56) References Cited

OTHER PUBLICATIONS

Advisory Action in U.S. Appl. No. 13/017,244 mailed Oct. 17, 2013.
Notice of Allowance in U.S. Appl. No. 13/954,778 mailed Oct. 21, 2013.
Non-Final Office Action in U.S. Appl. No. 13/962,893 mailed Oct. 22, 2013.
Non-Final Office Action in U.S. Appl. No. 13/975,215 mailed Oct. 23, 2013.
Interview Summary in U.S. Appl. No. 13/017,244 mailed Oct. 25, 2013.
Non-Final Office Action in U.S. Appl. No. 13/975,215 mailed Nov. 12, 2013.
Non-Final Office Action in U.S. Appl. No. 13/975,223 mailed Nov. 12, 2013.
Non-Final Office Action in U.S. Appl. No. 13/975,234 mailed Nov. 13, 2013.
Peters et al., "Accurate whole-genome sequencing and haplotyping from 10 to 20 human cells", Nature. Jul. 11, 2012;487(7406):190-5.
Bader et al., "The Relative Power of SNPs and Haplotype as Genetic Markers for Association Tests," Pharmacogenomics, 2(1):11-24 (2001).
Baumann, "Determination of Haplotypes from Genotype Information," Informatik, ETH Zurich, 2005, 15 pages.
Li et al., "Haplotype Reconstruction from SNP Alignment," Journal of Computational Biology, 11(2-3):507-518 (2004).
Examiner's Report for CA Application No. 2,611,743, mailed Dec. 2, 2016, 5 pages.
Cai et al., "A clone-array pooled shotgun strategy for sequencing large genomes", Genome Research, 2001, 11, pp. 1619-1623.
Extended European Search Report received in European Patent Application No. 17167651.3. Dated Sep. 11, 2017. 16 pages.

* cited by examiner

SEQUENCE LISTING

```
<160> NUMBER OF SEQ ID NOS: 7

<210> SEQ ID NO 1
<211> LENGTH: 80
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: n can be any one of A, C, T or G
<220> FEATURE:
<221> NAME/KEY: misc_feature
<222> LOCATION: (14)..(14)
<223> OTHER INFORMATION: n can be any one of A, C, T or G
<220> FEATURE:
<221> NAME/KEY: misc_feature
```

```
<222> LOCATION: (20)..(20)
<223> OTHER INFORMATION: n can be any one of A, C, T or G
<220> FEATURE:
<221> NAME/KEY: misc_feature
<222> LOCATION: (26)..(26)
<223> OTHER INFORMATION: n can be any one of A, C, T or G
<220> FEATURE:
<221> NAME/KEY: misc_feature
<222> LOCATION: (32)..(32)
<223> OTHER INFORMATION: n can be any one of A, C, T or G
<220> FEATURE:
<221> NAME/KEY: misc_feature
<222> LOCATION: (47)..(47)
<223> OTHER INFORMATION: n can be any one of A, C, T or G
<220> FEATURE:
<221> NAME/KEY: misc_feature
<222> LOCATION: (53)..(53)
<223> OTHER INFORMATION: n can be any one of A, C, T or G
<220> FEATURE:
<221> NAME/KEY: misc_feature
<222> LOCATION: (67)..(67)
<223> OTHER INFORMATION: n can be any one of A, C, T or G
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (73)..(80)
<223> OTHER INFORMATION: n can be any one of A, C, T or G

<400> SEQUENCE: 1
nnnnnnnngc atancacgan gtcatnatcg tncaaacgtc agtccangaa tcnagatcca      60
cttagantgn cgnnnnnnnn                                                 80

<210> SEQ ID NO 2
<211> LENGTH: 50
<212> TYPE: DNA
<213> ORGANISM: Artificial sequence
<220> FEATURE:
<223> OTHER INFORMATION: Synthetic oligonucleotide

<400> SEQUENCE: 2
tatcatctgg atgttaggaa gacaaaagga agctgaggac attaacggac                50

<210> SEQ ID NO 3
<211> LENGTH: 15
<212> TYPE: DNA
<213> ORGANISM: Artificial sequence
<220> FEATURE:
<223> OTHER INFORMATION: Synthetic oligonucleotide

<400> SEQUENCE: 3
accttcagac cagat                                                      15

<210> SEQ ID NO 4
<211> LENGTH: 25
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(7)
<223> OTHER INFORMATION: n can be any one of A, C, T or G

<400> SEQUENCE: 4
nnnnnnngtc cgttaatgtc ctcag                                           25

<210> SEQ ID NO 5
```

```
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (16)..(22)
<223> OTHER INFORMATION: n can be any one of A, C, T or G

<400> SEQUENCE: 5
atctggtctg aaggtnnnnn nn                                              22

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
cttttgtctt cctaacatcc                                                 20

<210> SEQ ID NO 7
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 7
agatgataat ctggtc                                                     16
```

PREPARING A DNA FRAGMENT LIBRARY FOR SEQUENCING USING TAGGED PRIMERS

RELATED APPLICATIONS

This application is a divisional of U.S. patent application Ser. No. 13/954,778, filed Jul. 30, 2013 (pending); and a divisional of U.S. patent application Ser. No. 13/017,244, filed Jan. 31, 2011 (pending).

U.S. patent application Ser. No. 13/954,778 is a divisional of U.S. patent application Ser. No. 13/017,244 (pending), filed Jan. 31, 2011; which is a continuation of U.S. patent application Ser. No. 12/335,168, filed Dec. 15, 2008, issued as U.S. Pat. No. 7,901,891 on Mar. 8, 2011; which is a continuation of U.S. patent application Ser. No. 11/451,692, filed Jun. 13, 2006, issued as U.S. Pat. No. 7,709,197 on May 4, 2010; which claims the priority benefit of U.S. Provisional Application Nos. 60/776,415, filed Feb. 24, 2006; 60/725,116, filed Oct. 7, 2005; and 60/690,771, filed Jun. 15, 2005.

Each of the aforelisted priority applications are hereby incorporated herein by reference in their entirety for all purposes.

GOVERNMENT INTERESTS

This invention was made with government support under grant No. 1 U01 AI057315-01 awarded by the National Institutes of Health. The government has certain rights in the invention.

FIELD OF THE INVENTION

The present invention relates to methods for determining nucleotide sequences and/or marker maps of large nucleic acids, such as genomes or parts of genomes, and more particularly, to methods for reconstructing sequences of large nucleic acids from sequences of many fragments thereof.

BACKGROUND

The goal set by National Human Genome Research Institute to promote the development of technology for sequencing mammalian-sized genomes for under $1000. was a dramatic acknowledgement of the tremendous value that nucleic acid sequence data has in virtually every area of the life sciences, Collins et al (2003), Nature, 422: 835-847. This challenge has spurred interest in many different sequencing approaches as alternative to, or complements of, Sanger-based sequencing, which has been the work-horse sequencing technology for the last two decades, e.g. Margulies et al (2005), Nature, 437: 376-380; Shendure et al (2005), Science, 309: 1728-1732; Kartalov et al, Nucleic Acids Research, 32: 2873-2879 (2004); Mitra et al, Anal. Biochem., 320: 55-65 (2003); Metzker (2005), Genome Research, 15: 1767-1776; Shendure et al (2004), Nature Reviews Genetics, 5: 335-344; Balasubramanian et al, U.S. Pat. No. 6,787,308; and the like. A common attribute of many of these new approaches is the acquisition of sequence information from many short randomly selected fragments in a highly parallel manner. Massive amounts of sequence information are generated that must be processed to reconstruct the sequence of the larger polynucleotide from which the fragments originated. Unfortunately such processing presents a significant hurdle to many genome sequencing projects because of the well-known difficulties of reconstructing long polynucleotides from short sequences, e.g. Drmanac et al, Advances in Biochem. Engineering, 77: 75-101 (2002).

Another difficulty faced by current and developing sequence technologies arises from the diploid nature of many organisms of interest. That is, the cells of all mammals and many other organisms of interest contain two copies of every genomic sequence and the pair of such sequences differ from one another by a small but significant degree due to natural allelic variation, mutations, and the like. Thus, when diploid genomes are reconstructed from shorter sequences, it is very difficult to determine which difference should be allocated to which sequence of the pair. A similar difficulty arises when sequencing populations of organisms as well, e.g. Tringe et al (2005), Nature Reviews Genetics, 6: 805-814. In the latter case, there are mixtures of pathogens (for example, HIV or other viruses) where complete viral or bacterial strain or haplotype determination is critical for identifying an emerging resistant organism or man-modified organism mixed with non-virulent natural strains.

In view of the above, it would be highly useful, particularly to many sequencing technologies under development, to have available a technique that would allow the generation of additional information about the location of short sequence reads in a genome.

SUMMARY OF THE INVENTION

The invention provides methods and kits for determining nucleotide sequences and/or marker maps of one or more target polynucleotides. In one aspect, the invention provides a method of characterizing nucleotide sequences of one or more target polynucleotides comprising the steps of: (a) forming a plurality of tiers of mixtures that comprise a hierarchy of nested fragments of the one or more target polynucleotides, each mixture of each prior tier being divided into a number of mixtures in a subsequent tier, at least one tier having mixtures with substantially non-overlapping fragments, and the plurality of tiers having a final tier wherein mixtures of prior tiers can be identified for each fragment of each mixture of the final tier; (b) determining sequence information from at least a portion of one or more fragments of each mixture in the final tier; and (c) providing complete or partial nucleotide sequences of the one or more target polynucleotides by ordering the sequence information from the final tier of mixtures, wherein such ordering depends on the identity of at least one mixture of at least one tier from which a fragment is derived that gives rise to a portion of such sequence information.

In another aspect, the invention provides a method of characterizing nucleotide sequences of one or more target polynucleotides comprising the steps of: (a) fragmenting the one or more target polynucleotides present in a predetermined coverage amount to form a population containing overlapping first-sized fragments each having an average length substantially less than those of the target polynucleotides; (b) forming a number of separate mixtures from the population of first-sized fragments, such number being selected such that substantially every first-sized fragment in a separate mixture is non-overlapping with every other first-sized fragment of the same mixture, and such that the mixture of origin of each such first-sized fragment can be identified; (c) determining sequence information from at least a portion of one or more first-sized fragments of each mixture; and (d) providing complete or partial nucleotide sequences of the one or more target polynucleotides by ordering the sequence information from the separate mixtures, wherein such ordering depends on the mixture of origin of at least a portion of the sequence information.

In still another aspect, the invention provides a method of preparing for sequence analysis one or more target polynucleotides present in a predetermined coverage amount, the method comprising the following steps: (i) fragmenting the one or more target polynucleotides to form a population containing overlapping first-sized fragments each having an average length substantially less than those of the target polynucleotides; (ii) aliquoting the population of first-sized fragments into a number of separate mixtures, such number being selected such that substantially every first-sized fragment in a separate mixture is non-overlapping with every other first-sized fragment of the same separate mixture; and (iii) attaching an oligonucleotide tag to each first-sized fragment in each separate mixture so that the oligonucleotide tag identifies the separate mixture of the first-sized fragment.

The invention further includes kits for implementing the methods of the invention. In one aspect, such kits comprise reagents and/or mechanical appliances for generating fragments of one or more target polynucleotides. In another aspect, such kits comprise reagents for attaching oligonucleotide tags to fragments generated from one or more target polynucleotides and divided into separate mixtures in accordance with methods of the invention.

DETAILED DESCRIPTION OF THE INVENTION

Figure 1A:
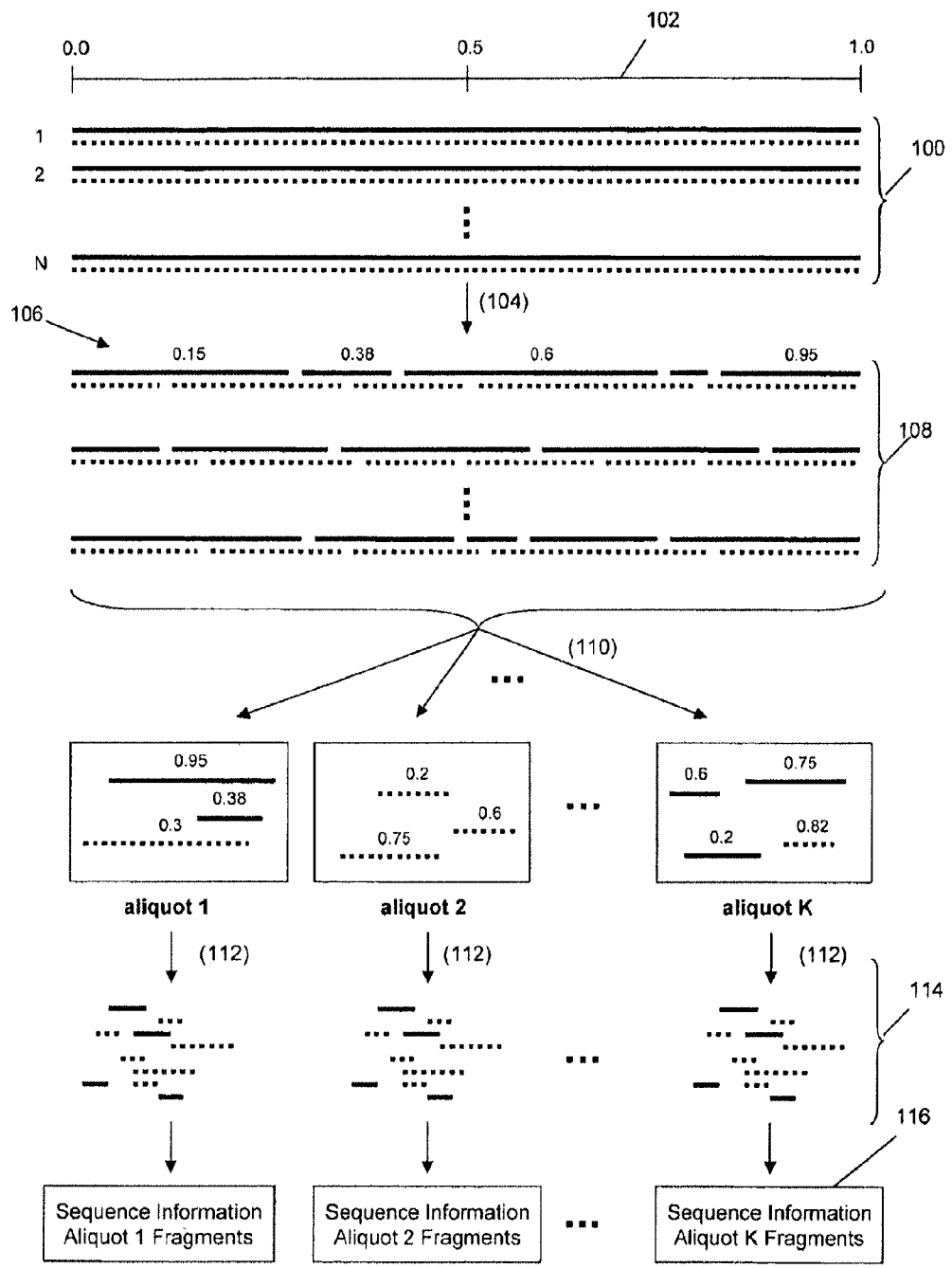
FIGS. 1A-1C illustrate different aspects of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual,* and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* 3$^{rd}$ Ed., W. H. Freeman Pub., New York, N.Y. and Berg et al. (2002) *Biochemistry*, 5$^{th}$ W. H. Freeman Pub., New York, N.Y., all of which are herein incorporated in their entirety by reference for all purposes.

The invention provides methods and kits for ordering sequence information derived from one or more target polynucleotides. In one aspect, one or more tiers or levels of fragmentation and aliquoting are generated after which sequence information is obtained from fragments in a final level or tier. Each fragment in such a final tier is from a particular aliquot, which, in turn, is from a particular aliquot of a prior level or tier. For every fragment of an aliquot in the final tier, the aliquots from which it was derived at every prior level is known. Thus, identical sequences from overlapping fragments from different aliquots can be distinguished and grouped as being derived from the same or different fragments from prior levels. When the fragments in the final tier are sequenced, overlapping sequence regions of fragments in different aliquots are used to register the different fragments so that non-overlapping regions are ordered. In one aspect, this process is carried out in a hierarchical fashion until the one or more target polynucleotides are characterized, e.g. by their nucleic acid sequences, or by an ordering of sequence segments, or by an ordering of single nucleotide polymorphisms (SNPs), or the like. In another aspect, fragments at each tier are tagged with an oligonucleotide tag to identify the tier and aliquot of the separate mixture, after which fragments of the final tier may be mixed (either to form a single mixture or multiple mixtures) and analyzed together, for example, by way of a high-throughput sequencing device, e.g. Margulies et al (2005), Nature, 437: 376-380; Shendure et al (2005), Science, 309: 1728-1732. The results of such sequencing is the acquisition of sequence information of final fragments coupled with identification of one or more oligonucleotide tags, which, in turn, identify fragments from prior tiers that a final fragment is derived from. Sequences of the tags, since they are selected from a known set, may also be used to improve base calling, or be used as a quality control measure for sequencing. Such tags may also mark the end sequences of longer fragments before subsequent fragmenting and may be used to guide sequence or map assembly. In one aspect, oligonucleotide tag may be added to fragments by replicating fragment using tagged primers; that is, primers that have a fragment binding portion, which may be a random sequence, e.g. 6 to 18 bases in length, and a portion (usually a 5' portion) that does not bind to fragments that contains an oligonucleotide tag.

Oligonucleotide tags are identified by their nucleotide sequences. Such identification may be accomplished as part of sequencing final tier fragments (that is, the nucleotide sequence determined includes the sequence of an oligonucleotide tag as well as the nucleotide sequence of a portion of a final tier fragments). Alternatively, sequences of oligonucleotide tags may be identified by hybridization probes, e.g. on a microarray.

A common feature in all applications of this invention (genome sequencing, SNP or other marker mapping or cDNA analysis) is aliquoting nucleic acid sample such that sequences of predetermined type of relatedness (overlapped fragment, fragments with high similarity, homologous chromosomes, messengers transcribed from the same gene) occur mostly once e.g. as a single molecule per aliquot.

Figure 1B:
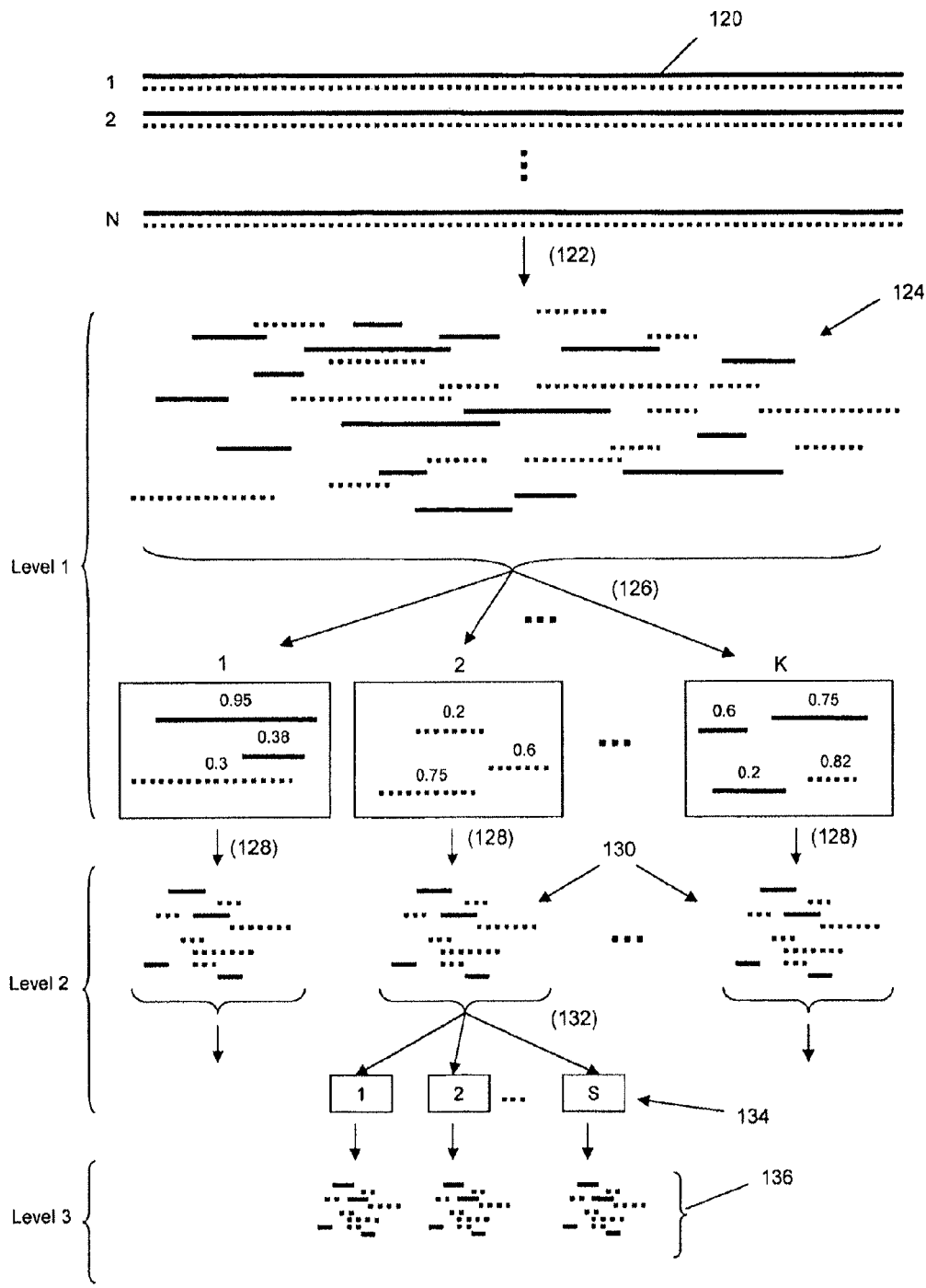

FIG. 1A provides an illustration of one aspect of the invention. N diploid genomes (100) are shown aligned prior to fragmentation below scale (102) that illustrates positions of fragments within the genomes by a number between 0 and 1. (That is, target polynucleotides (100) are present in a coverage amount of "2N.") After fragmentation (104) each genome is broken into multiple overlapping fragments that co-exist in one mixture (108), where fragments of one strand of top-most genome (106) (solid lines) are label by their position in the genome. Fragments of mixture (108) are then divided into a number of aliquots 1 through K such that the likelihood of any one aliquot receiving overlapping fragments is small, e.g. less than one percent. (Many or all aliquots may have one or a few pairs of overlapped fragments, but any given segment of a polynucleotide or a pair or a group of multiple related/homologous polynucleotides is represented in most of the aliquots (e.g., >90%) by a single thus non-overlapping fragment. If there are two overlapping fragments from a polynucleotide in one aliquot they appear as one longer fragment. Only non-overlapped segments of two overlapped fragments one from each parental chromosome would provide haplotype information.) In one aspect, minimal overlapping of fragments insures that the fragments can be unambiguously sequenced without confounding affects caused by the presence of substantially overlapping fragments that may contain small differences, such as may be found whenever heterozygous parental strands are present or whenever strands of a mixed-strain population of microbes are present. Usually, after fragmentation either before or after formation of separate mixtures, the fragments are replicated in order increase the amount of target material for analysis. In one aspect, fragments are replicated after the have been separated into separate mixtures using a conventional replication technique that does not bias the amounts of different sequences amplified. In one aspect, such first tier fragments are further fragmented (112) within their respective aliquots to form a second tier of fragments (114). Usually, prior to fragmentation (112), fragments of each aliquot may be replicated using a conventional DNA replication process, such as whole genome amplification using random primers and a highly processive DNA polymerase with strand displacement activity, e.g. U.S. Pat. No. 6,617,137, which is incorporated herein by reference. Preferably the replication method does not bias the relative amounts of each fragment. It is understood that replication by some methods will reduce the average fragment length. Second tier fragments (114) are then analyzed by any number of analytical assays, as noted above. Preferably, second tier fragments (114) are analyzed by a highly parallel DNA sequencing method, such as the one described more fully below, or like method. As noted above, the steps of fragmenting and aliquoting may be carried out multiple times, as illustrated in FIG. 1B, to generate multiple levels or tiers of fragments. There, target polynucleotide (120) present in coverage amount 2N is fragmented (122) to form mixture (124), which is then separated (126) into aliquots 1 through K. As above, K is selected to minimize the probability of having overlapping fragments within the same aliquot. Fragments of each aliquot are replicated then further fragmented (128) to form a second tier or level of fragments (130). Fragments from each aliquot of the second tier may then be further divided (132) into aliquots (134) and again replicated and fragmented to form a third tier or level of fragments (136). In FIG. 1B, third tier aliquots (1 through S) and fragments are shown only for fragments derived from aliquot 2 of the first level.

In one aspect of the invention, only a single level of fragmenting is carried out. A method for characterizing nucleotide sequences of one or more polynucleotides that exemplifies this aspect is carried out with the following steps: (i) fragmenting the one or more target polynucleotides present in a predetermined coverage amount to form a population containing overlapping first-sized fragments each having an average length substantially less than those of the target polynucleotides; (ii) forming a number of separate mixtures from the population of first-sized fragments, such number being selected such that substantially every first-sized fragment in a separate mixture is non-overlapping with every other first-sized fragment of the same mixture and such that the mixture of origin of each such first-sized fragment is determinable; (iii) determining sequence information from at least a portion of one or more first-sized fragments of each mixture; and (iv) providing complete or partial nucleotide sequences of the one or more target polynucleotides by ordering the sequence information from the separate mixtures, wherein such ordering depends on the mixture of origin of at least a portion of the sequence information. As with other methods of the invention, mixtures from which a fragment is derived can be determined by attaching an oligonucleotide tag to each fragment in a mixture, as discussed more fully below.

In one aspect, sequence information from fragments is in the form of sequence reads. That is, sequence information comprises a nucleotide sequence of a portion of a fragment, frequently an end of a fragment. The length of such sequence reads depends on the sequencing technique used to analyze the fragments. In one aspect, sequence reads have lengths in the range of from 12 to 600 bases; and in another aspect, sequence reads have lengths in the range of from 20 to 100 bases; or in the range of from 20 to 50 bases. For each separate mixture, a number of sequence reads are acquired so that sequences of the fragments of the mixtures are substantially covered, i.e. represented in the number sequence reads. Clearly, the larger the number of sequence reads the greater the likelihood that the sequences are covered by a given amount or percentage. In one aspect, substantially covered means that at least 30 percent of such sequences are covered; or at least 50 percent covered; or at least 66 percent covered; or at least 75 percent covered.

In one aspect, sequence reads are determined from concatemers of fragments, as described more fully below, using the following steps: (i) generating for each separate mixture a plurality of target concatemers from the first-sized fragments, each target concatemer comprising multiple copies of a portion of a first-sized fragment and each plurality of target concatemers including a number of such portions that substantially covers the first-sized fragment; (ii) forming for each of the separate mixtures a random array of target concatemers fixed to a surface at a density such that at least a majority of the target concatemers are optically resolvable; and (iii) generating a number of sequence reads from target concatemers of each of said separate mixtures, such sequence reads each having a length substantially less than those of said first-sized fragments, and each of such numbers of sequence reads being selected such that the sequences reads of each said separate mixture substantially covers said first-sized fragments therein. In regard to selecting a plurality of concatemers so that the one or more target polynucleotides are covered, the degree of coverage depends in part on the type of analysis being undertaken. For example, for determining the complete nucleotides sequences of the one or more target polynucleotides, the degree of coverage usually at least two time, or more usually at least five times, the total length of the one or more target polynucleotides, e.g. Waterman, Introduction to Computational Biology: Maps, Sequences and Genomes (Chapman & Hall/CRC, 1995); Lander et al, Genomics, 2: 231-239 (1988); and the like. For partial sequence analysis, e.g. ordering methylation-rich regions, a lesser degree of coverage may be sufficient. In regard to selecting a number of sequence reads to substantially cover fragments in a mixture, usually the degree of coverage is less than 100 percent, as noted above.

In another aspect, sequence information from fragments is in the form of the presence or absence of given polymorphisms, such as single nucleotide polymorphisms (SNPs), which may be measured by a variety of methods, e.g. Syvanen (2005), Nature Genetics Supplement, 37: S5-S10; Gunderson et al (2005), Nature Genetics, 37: 549-554; Fan et al (2003), Cold Spring Harbor Symposia on Quantitative Biology, LXVIII: 69-78; and U.S. Pat. Nos. 4,883,750; 6,858,412; 5,871,921; 6,355,431; and the like, which are incorporated herein by reference. In one aspect, sequence information comprises the determination of the presence or absence in each separate mixture of at least 5 SNPs, or at least 10 SNPs, or at least 30 SNPs, or at least 50 SNPs, or at least 100 SNPs.

Implementing the invention involves several design choices within the purview of those of ordinary skill. Such design choices include selecting the following parameters: fragment sizes at each level, coverage amount of target polynucleotides, number of aliquots at each level, number of levels, type of sequence information to obtain, the degree and method of fragment replication at each level, and the like. Typically, after extraction and/or purification by conventional means, DNA or RNA is fragmented enzymatically or mechanically. Preferably, target polynucleotides are randomly fragmented so that overlapping fragments are produced. At each level after fragmentation, the reaction mixture containing the fragments is divided into multiple separate mixtures. This may be done by dividing the mixture into aliquots. Or, alternatively, portions of the reaction mixture may be separated into separate mixtures such that not all of the original reaction mixture is used. Usually, the mixture is divided into a number of equal sized aliquots. A number of aliquots (or separate mixtures) is selected so that there is only a minimal probability that the fragments in such mixtures overlap (or maximally tolerable to reduce cost of handling large number of aliquots). In one aspect, a number of separate mixtures is selected so that the probability of overlapping fragments is less than 10%; in another aspect, less than 5%; in another aspect, less than 1%; in still another aspect, less than 0.1%; and in another aspect, less than 0.01%. In another aspect, a number of separate mixtures is selected so that at least sixty percent of such separate mixtures contain only non-overlapping fragments; or in another aspect, a number of separate mixtures is selected so that at least eighty percent of such separate mixtures contain only non-overlapping fragments; or in another aspect, a number of separate mixtures is selected so that at least ninety percent of such separate mixtures contain only non-overlapping fragments. Clearly, the number of separate mixtures or aliquots to achieve a given probability depends on the coverage amount of target polynucleotide used in the method. "Coverage amount" means a factor times the amount of nucleic acid equivalent to one copy of the target polynucleotides. For example, 1 ng of human genomic DNA is equivalent to about 300 copies of a haploid human genome. Thus, a coverage amount of 300 for a human haploid genome as a target polynucleotide is 1 ng. Aliquoting or creating separate mixtures may be done by conventional pipetting into conventional laboratory vessels, such as, tubes or all or some of the wells of one or more 96-well, or 384-well, or 1536-well plates. In one aspect, coverage amounts are in the range of from 2 to 50, or in the range of from 5 to 40, or in the range of from 5 to 30, or in the range of from 5 to 20. In one aspect, target polynucleotide DNA is randomly fragmented using conventional methods including, but not limited to, sonication, passage through capillaries, dispersion of DNA solution into fine drops, treatment with DNase I, treatment with endonuclease, tagged PCR amplification, and the like, e.g. Dienenger (1983) Anal. Biochem., 129: 216-223; Schriefer et al (1990), Nucleic Acids Research, 18: 7455; Anderson et al (1996) Anal. Biochem., 236: 107-113; Anderson et al (1981) Nucleic Acids Research, 9: 3015-3027; Fitzgerald et al (1992) Nucleic Acids Research, 20: 3753-3762; Grothues et al, Nucleic Acids Research, 21: 1321-1322; Zheleznaya et al (1999), Biochemistry (Moscow) 64: 373-378; and the like. It is understood that in some instances target polynucleotides are fragmented in the course of conventional extractions methods, so that, in particular, an initial step of fragmenting may simply result from conventional extraction and handling of target polynucleotides, e.g. mammalian genomic DNA, or the like. Average fragment size may be selected in each of these methods by routine parameter choices. In one aspect, four levels of fragmentation are implemented wherein fragments of the first fragmentation, i.e. first-sized fragments, are in a range of from 100-300 kilobases (kb), fragments of the second fragmentation, i.e. second-sized fragments, are in a range of from 10-30 kilobases (kb), fragments of the third fragmentation, i.e. third-sized fragments, are in a range of from 1-3 kilobases (kb), and fragments of the fourth or final fragmentation, i.e. final-sized fragments, are in a range of from 50-600 bases. In another aspect, average fragment sizes are selected relative to the length of the target polynucleotides. Thus, for example, selecting average fragment sizes substantially less than those of fragments from the prior tier means selecting an average size less than one third the size of the average size of fragments of the prior tier; or in another aspect, selecting an average size less than one tenth the size of the average size of fragments of the prior tier; or in another aspect, selecting an average size less than one thirtieth the size of the average size of fragments of the prior tier; or in another aspect, selecting an average size less than one hundredth the size of the average size of fragments of the prior tier; or in another aspect, selecting an average size less than one thousandth the size of the average size of fragments of the prior tier.

In one aspect, having a subset of aliquots with much fewer fragments than the others is useful for sequence reconstruction. That is, instead of dividing a mixture of fragments into equal volume separate mixtures, which on average would result in equal numbers of fragments in each separate mixture, a mixture of (for example) first-sized fragments may be divided into separate mixtures that include subsets with fewer fragments. For human genome, for example, if a mixture is divided into only 384 separate mixtures, a subset of 96 such mixtures may have only about four hundred 100 kb fragments each and the other 3×96 separate mixtures may have about four thousand 100 kb fragments each. The low complexity separate mixtures (~40 Mb of genomic DNA) may be used to simplify sequence assembly especially for de-novo analysis. Sequences from such low complexity separate mixtures may be used to find all other sequences in high complexity aliquots that overlap with them and thus form low complexity subsets from the large set of about 6 billion generated sequence reads. The low complexity sets allows more efficient final sequence assembly. If more separate mixtures are formed, such as 1536 (especially efficient by tagging second-sized fragments), then 384 or 2×384 aliquots may have only fifty to one hundred 100 kb fragments representing only 5-10 Mb of genomic DNA.

In another aspect, having an initial population of long fragments that are highly overlapped provides the best conditions to assemble parental chromosomes. For 20× and 100 kb fragments, the neighboring fragments will have 95 kb overlap, on average. 20× coverage will also assure that in large majority of cases the overlap of consecutive fragments is at least 10 kb (e.g having about 10 SNPs that differentiate two parental chromosomes).

As mentioned above, in one aspect, the invention provides a method of characterizing nucleotide sequences of one or more target polynucleotides comprising the steps of: (a) forming one or more tiers of mixtures that comprise a hierarchy of nested fragments of the one or more target polynucleotides, each mixture of each prior tier being divided into a number of mixtures in a subsequent tier so that at least one tier has mixtures with substantially non-overlapping fragments, and the one or more tiers having a final tier wherein mixtures of prior tiers can be identified for each fragment of each mixture of the final tier; (b) determining sequence information from at least a portion of one or more fragments of each mixture in the final tier; and (c) providing complete or partial nucleotide sequences of the one or more target polynucleotides by ordering the sequence information from the final tier of mixtures, wherein such ordering depends on the identity of at least one mixture of at least one tier from which a fragment is derived that gives rise to a portion of such sequence information. In one aspect, the number of tiers is one; and in another aspect, the number of tiers is two; and in further aspects, the number of tiers may be a plurality greater than two. For example, the plurality may be three, or it may be four. As used herein, the term "hierarchy of nested fragments" means levels (or equivalently, tiers) of fragmentation wherein the levels are related in that fragments of each successive level are derived from the fragments from an immediately prior level. Moreover, fragments derived from an immediately prior level have average lengths that are substantially less than those of the fragments from which they are derived; hence, they are nested in that sense. The nature and origin of the one or more target polynucleotides may vary widely. The one or more target polynucleotides may comprise mRNAs or cDNAs, or they may comprise whole genomes or fragments of genomes. One or more target polynucleotides may be one or more bacterial genomes, or one or more fungal genomes, or one or more mammalian genomes, or one or more plant genomes, or fragments of any of the preceding. In another aspect, one or more target polynucleotides may comprise one or more strains or species of bacterial or viral genomes. In still another aspect, one or more target polynucleotides may comprise one or more genomes or genome fragments from a community of organisms, such as enteric bacterial, vaginal microorganisms, or the like.

As mention above, sequence information may be derived from many different types of analysis, such as, SNP measurements, nucleotide sequence determination, determination of methylated bases, restriction sites, DNA binding sites, and the like. In one aspect, sequence information comprises nucleotide sequence determination of at least a portion of substantially every final fragment. Such information can be obtained by any of the available sequencing techniques, but those that are amenable to convenient highly parallel sequencing of many hundreds or thousands, or hundreds of thousands, or millions of fragments simultaneously are preferred. Such techniques may provide nucleotide sequences of varying lengths, i.e. they may have differing "read lengths." In one aspect, read lengths of from 10 to 500 are obtained; or read lengths of from 20 to 100 are obtained. In other aspects, sequence information is obtained from multiple levels in a single operation, so that for example, a number of fragments from a first tier may be sequenced with a first technique that provides read lengths in a range of from 100 to 1000 nucleotides, whereas another number of fragments (usually greater than the first number) are sequenced with a second technique that provides read lengths in the range of from 20 to 100 nucleotides. After such sequence information is obtained, assembling such information to reconstruct the sequences of fragments within an aliquot or of fragments or contigs within the sample is well-known, as evidenced by the following exemplary references that are incorporated by reference: Waterman, Introduction to Computational Biology: Maps, Sequences and Genomes (Chapman & Hall/CRC, 1995); Pevzner, Computational Molecular Biology: An Algorithmic Approach (MIT Press, 2000); Drmanac, R., Labat, I., Crkvenjakov, R., J. Biomol. Struct. Dyn., 5: 1085, (1991); Reinert et al, J. Comput. Biol., 7: 1-46 (2000); Indury et al, J. Comput. Biol., 2: 291-306 (1995); Port et al, Genomics, 26: 84-100 (1995); Waterman, Bull. Math. Biol., 56: 743-767 (1994); Vingron et al, J. Mol. Biol., 235: 1-12 (1994); Churchill et al, Genomics, 14: 89-98 (1992); Lander et al, Genomics, 2: 231-239 (1988); Fleischmann et al, Science, 269: 496-512 (1995); and the like. In accordance with the method of the invention, ordering sequence information obtained from final fragments depends on the identity of at least one mixture of at least one tier from which a final fragment is derived that gives rise to a portion of such sequence information. In one aspect, ordering such information depends on a plurality of identifications of tiers and mixtures; and in another aspect, ordering such information depends on identifying each mixture and each tier from which a final fragment is derived that provides sequence information.

In another aspect, as mentioned above, two tiers or levels are created to assist in ordering sequence information in one or more target polynucleotides, which is implemented with the following steps: (a) fragmenting the one or more target polynucleotides present in a predetermined coverage amount to form a population containing overlapping first-sized fragments each having an average length substantially less than those of the target polynucleotides; (b) forming a number of separate mixtures from the population of first-sized fragments, such number being selected such that substantially every first-sized fragment in a separate mixture is non-overlapping with every other first-sized fragment of the same mixture; (c) fragmenting each of the first-sized fragments in each of the mixtures to form a population of second-sized fragments for each mixture such that each second-sized fragment has an average length substantially less than those of the first-sized fragments and such that the mixture of origin of each such second-sized fragment can be identified; (d) determining sequence information from at least a portion of one or more second-sized fragments of each mixture; and (e) providing complete or partial nucleotide sequences of the one or more target polynucleotides by ordering the sequence information from the aliquots, wherein such ordering depends on the mixture of origin of at least a portion of the sequence information. In one aspect, steps of fragmenting may include a step of separating the resulting fragments by size for more efficient further processing or so that subsequent aliquots contain different average sized fragments, which can provide further useful ordering information, for example, if larger fragments are end-sequenced to provide sequence segments with a known separation in the one or more target polynucleotides.

In one aspect, the methods of the invention provide physical maps of all DNA present in the sample. If the sample has one bacterial species, e.g. one bacterial chromosome then the method provides long range map for that chromosome. If the sample has two bacterial strains, the method provides a map for both of them. Similarly the method provides a map of both parental sets of chromosomes in diploid genomes. Because genomic sequences usually have many repeats (including duplicated genes or exons or other functional elements) physical mapping with high resolution and long range is critical for complete unambiguous sequence assembly. For genomes with larger numbers of dispersed repeats longer than the sequence read length fragment lengths can adjusted so that there are more fragments or more levels of fragmenting. By being able to assemble separately parental chromosomes in diploid genomes, haplotype information is obtained. In one aspect, the more similar the parental genomes are the longer initial fragment size is required to be able to assemble them separately. For example if the difference between parental chromosomes is 1 in 100,000 bases, then fragments close to 1 mb in size would be used.

In another aspect of fragmentation, instead of having a single optimal DNA fragment length, a more informative approach may consist of having, for example, 10× coverage in, for example, 100-200 kb and 10× coverage in 30-50 kb fragments. For maximal informativeness each fragment preparation may be processed separately in their own set of tubes or well-plates. Another approach is to start with, for example, 20× of, for example, 200 kb long fragments distributed in say 96-wells. This assures independence of ~40 fragments (20 from each parental chromosome) that overlap a given 200 kb fragment. For human genomes, each well will have about 6×20 Gb/200 kb/96 wells=~10,000 200 kb fragments covering 20% of each parental genomes. These fragments can be further fragmented to 10-30 kb fragments and then further aliquoted, for example, each original well into 4 new wells. This fragmenting and aliquoting step provides high frequency DNA brakes and reduces complexity of DNA per well, which are both needed for efficient mapping of frequent repeats, but preserves 200 kb information (it is known which 4 final wells map to each initial well) needed for assembly of parental chromosomes or similar bacterial genomes present in an environmental sample. This represents a three level fragmenting process.

In another aspect, the following is an example of using hierarchical DNA fragmentation and standard shotgun sequencing of clones. First-sized fragments are subjected to "whole DNA" amplification method such as RCA to provide amplification in the range of 1000-100,000 fold. The resulting DNA may be shorter than first-sized fragments. The resulting DNA is subjected to second fragmentation step using nucleases such as DNAse I or mechanical fragmentation to generate second-sized fragments in the range of 30-3000 bases. Second-sized fragments are "cloned", e.g. ligated into a plasmid vector. Each aliquot uses a vector that has different tag sequence, or an adapter with such sequence is first ligated to second-sized fragments. The resulting DNA is mixed from some or all wells and transformed into host cells, resulting into individual colonies harboring one cloned second-sized fragment. A set of colonies that provides at least about one fold coverage (and preferably 3-6 fold coverage) of the first-sized fragments is collected, prepared for sequencing, and sequenced using dideoxy sequencing technology. The sequencing primer(s) and reaction are adjusted to successfully read tag sequence in addition to at least one portion of the second-sized fragment. The resulting sequences are grouped by the tag and sequence contigs assembled in de-novo sequencing or are used to define a reference sequence for first-sized fragments in DNA re-sequencing applications. Overlapped sequence contigs from independent aliquots are used to assemble longer contigs to generate complete sequence or scaffolds of the genomic DNA present in the sample.

In one aspect, the methods of the invention use short and medium sequence read length of massively parallel sequencing technologies to construct maps or orderings of such short reads in target polynucleotides. In another aspect, preparing fragments in accordance with the invention in essence allows one to convert a short read length sequencing technique into long read length technique. That is, by aliquoting fragments so that the resulting fragments can be fully reconstruct from the short read lengths available, the reconstruct fragments can be used, in turn, to reconstruct fragments from the next higher level in a hierarchy.

For genomic sequencing using short read length techniques, it is important to incorporate effective mapping strategies to locate the short reads to the full genome of the organism. This is especially important for analysis of complex diploid genomes, de novo sequencing, and sequencing mixtures of bacterial genomes. The hierarchical fragmentation procedure addresses this issue. It may also aid in predicting protein alleles and to map short reads to the correct positions within the genome. Another example is the correct assignment of a mutation in a gene family if it occurs within ~100b DNA sequence shared between multiple genes. This method represents an enabling technology that provides mapping information for assembling chromosomal haplotypes for any sequencing method based on random DNA fragmentation. In this method, genomic DNA is first isolated as 30-300 kb sized fragments. Through proper dilution, a small subset of these fragments are, at random, placed in discrete wells or multi-well plates or similar accessories. For example a plate with 96, 384 or 1536 wells can be used for these fragment subsets. An optimal way to create these DNA aliquots is to isolate the DNA with a method that naturally fragments to high molecular weight forms, dilute to 10-30 genome equivalents after quantitation, and then split the entire preparation into 384 wells. This should result in a satisfactory representation of all genomic sequences, but performing DNA isolation on 10-30 cells with 100% recovery efficiency would assure that all chromosomal regions are represented with the same coverage. A goal of aliquoting is to minimize cases where any two overlapping fragments from the same region of a chromosome are placed in the same plate well. For diploid genomes represented with 10× coverage, there are 20 overlapping fragments on average to separate in distinct wells. If this sample was then distributed over a 384 well plate, then each well would contain, on average, 1,562 fragments. By forming 384 fractions in a standard 384-well plate there may only be about a 1/400 chance that two overlapping fragments may end up in the same well. Even if some matching fragments are placed in the same well, the other overlapping fragments from each chromosomal region may provide the necessary unique mapping information. The prepared groups of long fragments may be further cut to the final fragment size of about 300 to 600 bases. To obtain 10× coverage of each fragment in a group, the DNA in each well may be amplified before final cutting using well-developed whole genome amplification methods. All short fragments from one well may then be arrayed (as described below) and sequenced on one separate unit array or in one section of a larger continuous matrix. A composite array of 384 unit arrays is ideal for parallel analysis of these groups of fragments. In the assembly of long sequences representing parental chromosomes, the algorithm may use the critical information that short fragments detected in one unit array belong to a limited number of longer continuous segments each representing a discreet portion of one chromosome. In almost all cases the homologous chromosomal segments may be analyzed on different unit arrays. Long (~100 kb) continuous initial segments form a tailing pattern and provide sufficient mapping information to assemble each parental chromosome separately as depicted below by relying on about 100 polymorphic sites per 100 kb of DNA. In the following example dots represent 100-1000 consecutive bases that are identical in corresponding segments.

```
Well 3      ......T........C..........C...G..........A.........
Well 20     ....C........T..........T ...A....... .G.........C...
Well 157           .......T. ...A...... ..G...    ...C........A...C...
Well 258          ...C..........C...G..........A.........T........G...T....
```

Wells 3 and 258 assemble chromosome 1 of Parent 1:

```
...T........C..........C...G..........A.........T........G... T
```

Wells 20 and 157 assemble chromosome 1 of Parent 2:

```
...C........T...... ..T...A..........G... ...C........A...C...
```

Random arrays (described below) prepared by two-level DNA fragmenting combine the advantages of both BAC sequencing and shotgun sequencing in a simple and efficient way.

The DNA may be isolated from cells by standard procedures such as the Qiagen Genomic-tip kit, or any other procedure that maintains intact fragments of approximately 30-300 kilobases in length. Pulse field gel electrophoresis may be used to demonstrate effective size distribution of DNA fragments of several sample preparation methods. Genomic derived DNA fragments of approximately 30-300 Kb in size and could be diluted to 10-20 genome equivalents of DNA in an aliquot. The DNA may be distributed over the wells of a 384 well plate. To confirm that the distribution process has worked, PCR may be used to demonstrate that on average, 10 positive wells are identified per genomic region. However, since there is only 1 target per well this may be below the level of sensitivity for many PCR assays, so random whole genome amplification methods may be applied to increase the initial copy number for PCR amplification.

Amplification of the single targets obtained in the chromosomal separation procedure may be required for subsequent procedures. To achieve this one may utilize existing, commercially available methods for whole genome amplification, preferably linear amplification methods may be used that produce 10-100 fold amplification. In effect, these procedures should not discriminate in terms of the sequences that are to be amplified but instead may amplify all sequences within the sample. Note that this procedure does not require intact amplification of entire 100 kb fragments. Amplification in the form of fragments as short as 1 kb is sufficient.

Although each well contains amplified DNA, the sequence complexity of each well hasn't changed from the original 150-300 megabases. The next phase is to further fragment amplified DNA into smaller fragments of approximately 300-600 bases in length. This may be achieved by DnaseI digestion or possibly sonication. The DNA samples may then be heated to generate single stranded DNA that is then ligated to the left and right adapter subunits while in the single stranded state. The DNA within each well of the 384 well plate may be precipitated by isopropanol to selectively precipitate the longer fragments while the shorter fragments and adapters remain in the solution phase. The re-suspended DNA can then be attached to streptavidin coated magnetic beads for subsequent enzymatic procedures.

In another aspect, for simplified preparation of 384 genome fractions is to prepare 384 initial adapters encoded with a different 5-mer or 6-mer sequence and use them in each of 384 wells. After the initial encoded adapter is ligated, DNA from all wells is mixed for further processing in a single tube including RCR. Instead of having 384 subarrays corresponding to 384-wells the same information would be extracted by sequencing 5-6 bases using an additional adapter adjacent to these 5-6 base.

In one aspect, methods of the invention are particularly useful in the assembly of target polynucleotides that contain repetitive sequence regions, or repeat sequences, whose lengths are greater that of the read length of the sequence analysis method being used, as illustrated in the following example. At the same time, having DNA fragments starting on average every 5 kb provide a high resolution physical map for accurate sequence assembly in the presence of dispersed repeats longer than the sequence read length. Consider this situation with 100 kb fragments covering a genomic region with 4 identical 500 base repeats:

```
M1 ---70 kb----500 b repeat  ----4 kb----500 b repeat -  ---6 kb----500 b-----20 kb---
M2 ---10 kb----500 b repeat  ----4 kb----500 b repeat -  ---6 kb----500 b-----30 kb ----500 b repeat ---49 kb----
M3                           ----3 kb----500 b repeat -  ---6 kb----500 b-----30 kb ----500 b repeat ---60 kb----
M4                                                       ---2 kb----500 b-----30 kb ----500 b repeat ---68 kb----
```

If the read length is less than 500 bases, without mapping information provided by 100 kb fragments we will not be able to assemble this part of the sequence. In the case of resequencing, if one of the repeats has a mutation we would not be able to tell which of the repeats is mutated. In the case of de-novo genome sequencing, we would not be able to determine the order of the sequence segments starting and ending with the repeat sequence. But having frequent beginnings and ends of long overlapped fragments that are sequenced independently the complete sequence information is obtained. In the above example, Fragment 1 ends before repeat 4, e.g. provides information which repeat is the last repeat in fragments 2-4. Fragment 3 tells which repeat is first in fragments 1 and 2. Finally, fragment 4 maps the order of repeat 2 and 3 in fragments 2 and 3. If fragment 4 started 2-3 kb downstream (e.g. if we do not have high coverage) we would not be able to map repeats 2 and 3.

For assembly of parental chromosomes we need long overlaps and for mapping repeats we need frequent brakes. There is an optimum of length for given genome coverage. For 20× coverage 50 kb fragments provide 4 times more brakes than 200 kb fragments (e.g 1.25 kb instead of 5 kb average length of informational fragments; informational fragments are sequence segments between neighboring beginnings or ends of overlapping physical genomics fragments; the average length of informational fragments is calculated by the following equation: fragment length/2× coverage, e.g. 200 kb/2×20=5 kb) and such 50 kb fragments at 20× coverage may have long enough overlaps (47.5 kb, on average; almost all consecutive overlaps >5 kb). Random fragmentation is simpler to get such frequent cutting of genomic DNA than to use 20 or more rare-cutter restriction enzymes.

For viral analysis, when the entire genome is 10-100 kb, an important goal is determining the actual sequence of strains, e.g. an emerging strain. Because there is no (or almost no) long repeats in short genomes fragmenting and overlaps many not be required. For bacterial genomes long overlaps (30-100 kb) are needed, if it is desired to assemble completely individual genomes of highly similar strains (one sequence difference at 1-10 kb). If the differences are more frequent, strain genomes can be assembled using shorter fragments, e.g. 10-30 kb, with shorter overlaps.

In one aspect of analyzing mixtures of bacterial genomes, aliquots may be made so that each aliquot contains one cell type, or a maximum of one cell. DNA can then be fragmented to ~100 kb in level 2, if that information is needed for the sequence assembly across repeats. Such an aliquoting strategy can be used, for example, for more accurate pathogen diagnostic for health or biodefense applications. Most of the time, pathogens (e.g. HIV or other virus) are present in mixtures, when complete viral or bacterial strain or haplotype determination is critical to spot an emerging resistant organism or man-modified organism mixed with non-virulent natural strains.

In another aspect of the invention, a method is provided for preparing for sequence analysis one or more target polynucleotides present in a predetermined coverage amount, such method comprising the following steps: (i) fragmenting the one or more target polynucleotides to form a population containing overlapping first-sized fragments each having an average length substantially less than those of the target polynucleotides; (ii) aliquoting the population of first-sized fragments into a number of separate mixtures, such number being selected such that substantially every first-sized fragment in a separate mixture is non-overlapping with every other first-sized fragment of the same separate mixture; and (iii) attaching an oligonucleotide tag to each first-sized fragment in each separate mixture so that the oligonucleotide tag identifies the separate mixture of the first-sized fragment.

Short Read Length Sequencing Technique Using Random Arrays

In one aspect, the present invention may be used with "short read length" sequencing techniques for analysis of long target polynucleotides. Of particular interest is a sequence analysis technique described below that makes use of a random array of DNA fragments derived from one or more target polynucleotides. It comprises the formation of one or more random arrays of single molecules that are concatemer of DNA fragments derived from one or more target polynucleotides. Such concatemers are disposed randomly on a surface of a support material, usually from a solution; thus, in one aspect, such concatemers are uniformly distributed on a surface in close approximation to a Poisson distribution. In another aspect, such concatemers are disposed on a surface that contains discrete spaced apart regions in which single molecules are attached. Preferably, concatemer sizes and compositions, preparation methods, and areas of such discrete spaced apart regions are selected so that substantially all such regions contain at most only one single molecule. Concatemers of DNA fragments are roughly in a random coil configuration on a surface and are confined to the area of a discrete spaced apart region. In one aspect, the discrete space apart regions have defined locations in a regular array, which may correspond to a rectilinear pattern, hexagonal pattern, or the like. A regular array of such regions is advantageous for detection and data analysis of signals collected from the arrays during an analysis. Also, concatemers confined to the restricted area of a discrete spaced apart region provide a more concentrated or intense signal, particularly when fluorescent probes are used in analytical operations, thereby providing higher signal-to-noise values. Concatemers are randomly distributed on the discrete spaced apart regions so that a given region usually is equally likely to receive any of the different single molecules. In other words, the resulting arrays are not spatially addressable immediately upon fabrication, but may be made so by carrying out an identification or decoding operation. That is, the identities of the concatemers are discernable, but not known. Concatemers have sizes may range from a few thousand nucleotides, e.g. 10,000, to several hundred thousand nucleotides, e.g. 100-200 thousand.

Figure 2A:
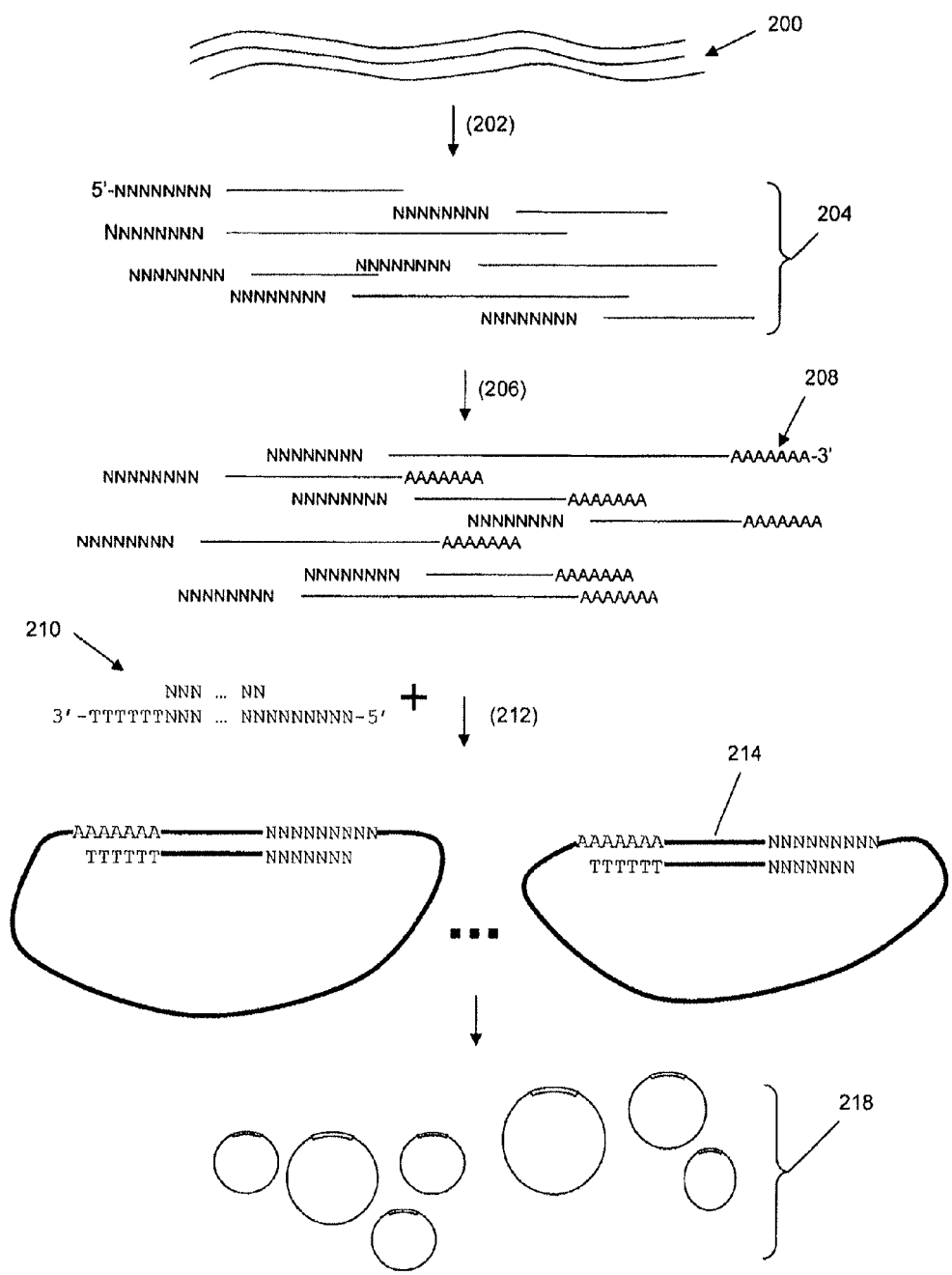
FIGS. 2A-2B illustrate methods of circularizing genomic DNA fragments for generating concatemers of polynucleotide analytes.
Figure 3A:
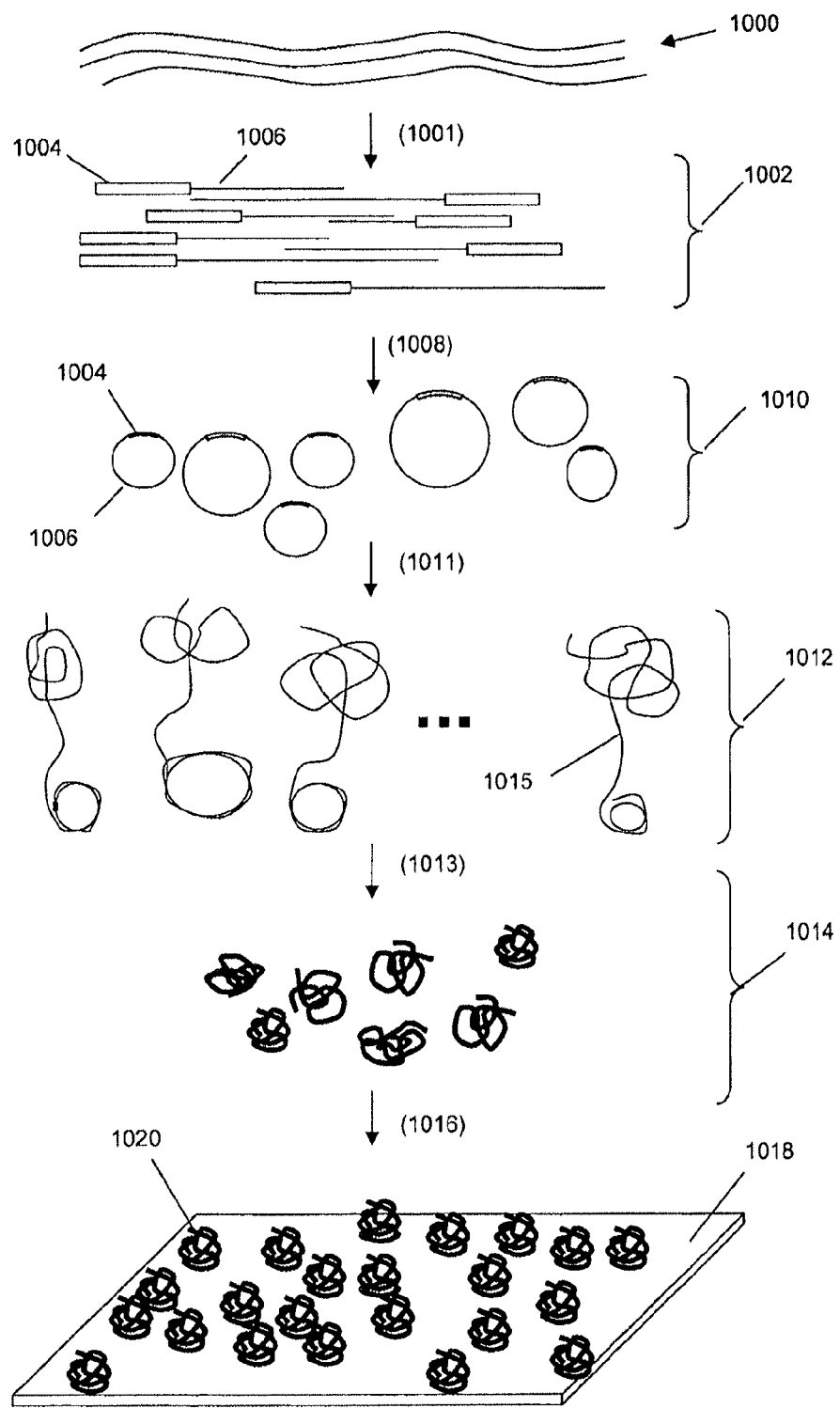
FIGS. 3A-3C illustrate a high-throughput sequencing method that may be used with the invention.
Figure 3B:
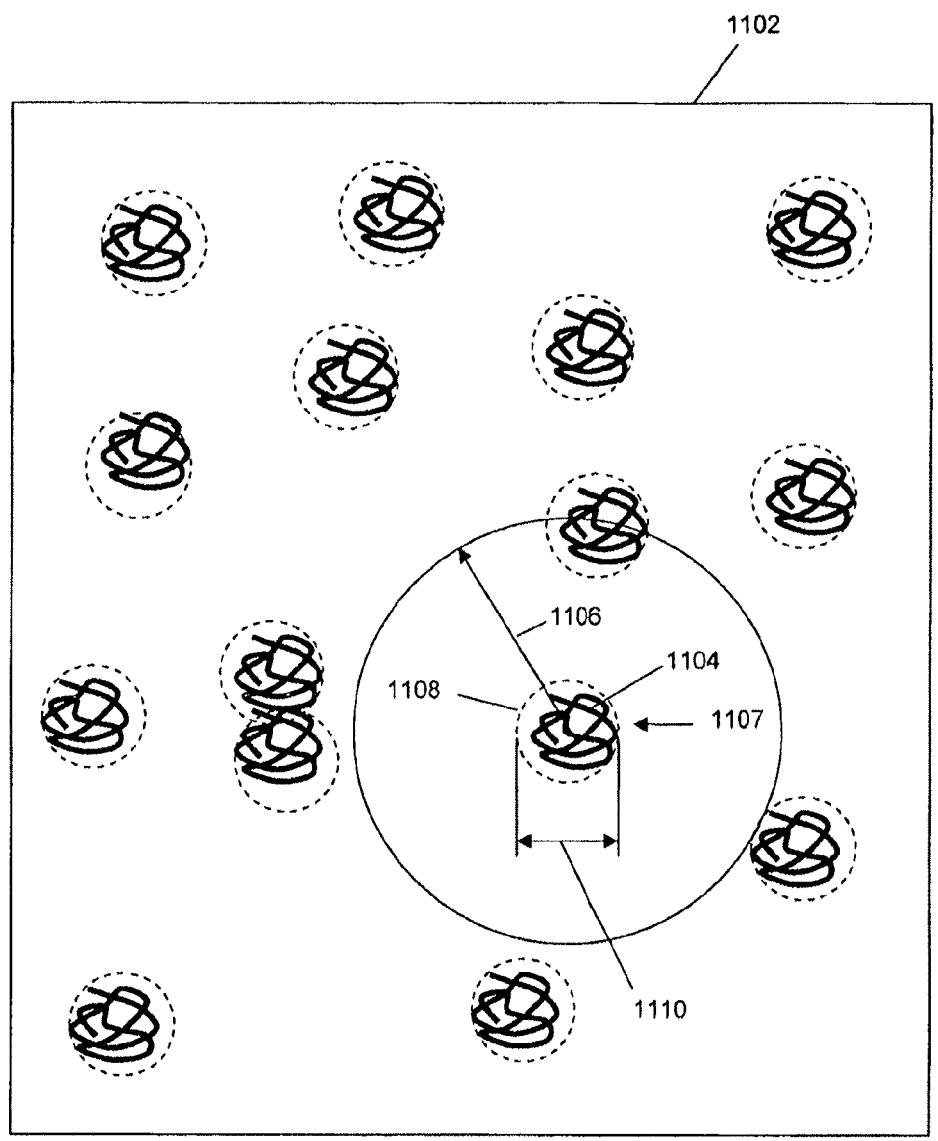
Figure 3C:
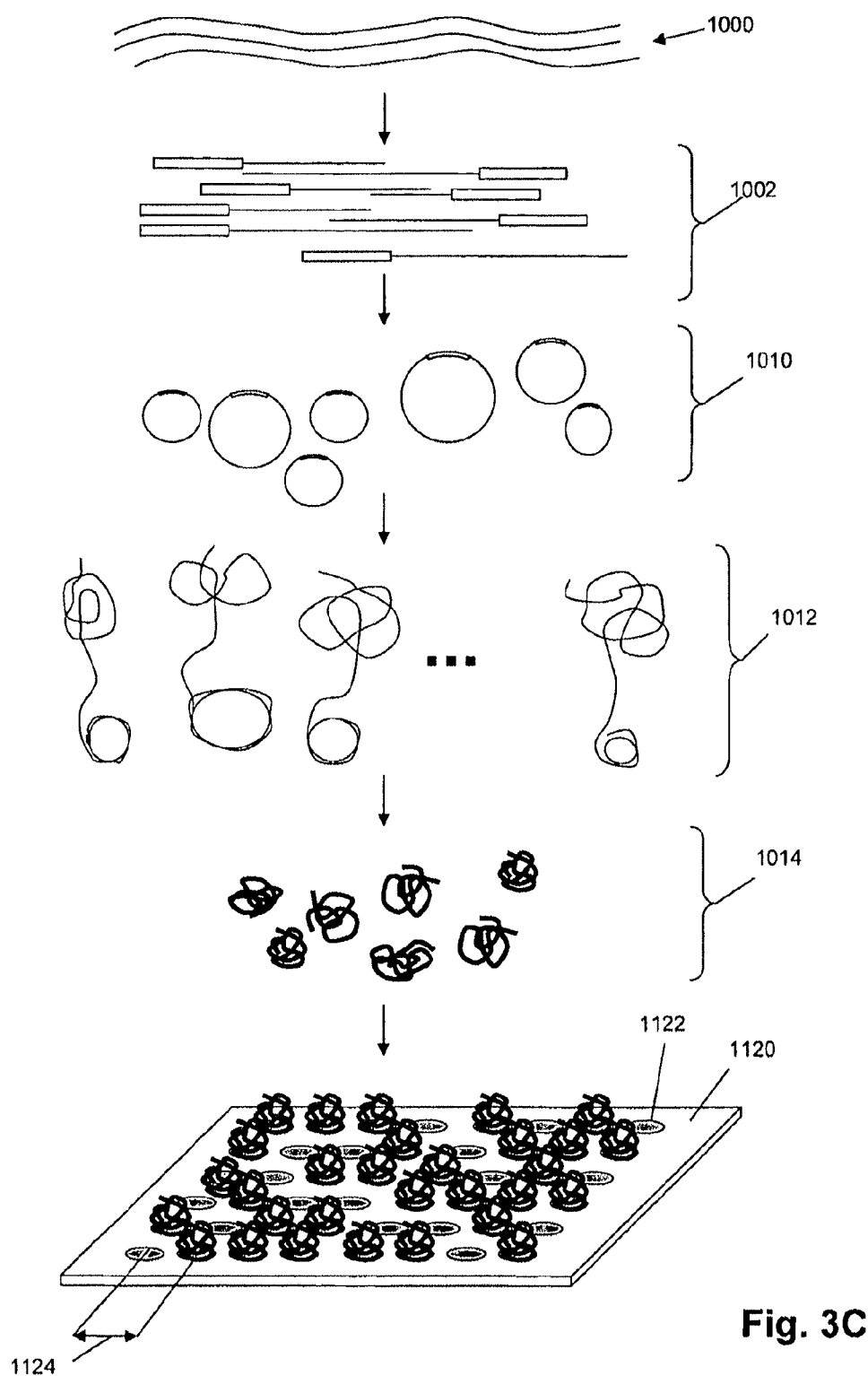

The above concepts are illustrated more fully in the embodiments shown schematically in FIGS. 3A-3C. After describing these figures, elements of the invention are disclosed in additional detail and examples are given. As mentioned above, in one aspect, macromolecular structures of the invention are single stranded polynucleotides comprising concatemers of a target sequence or fragment. In particular, such polynucleotides may be concatemers of a target sequence and an adaptor oligonucleotide. For example, source nucleic acid (1000) is treated (1001) to form single stranded fragments (1006), preferably in the range of from 50 to 600 nucleotides, and more preferably in the range of from 300 to 600 nucleotides, which are then ligated to adaptor oligonucleotides (1004) to form a population of adaptor-fragment conjugates (1002). Source nucleic acid (1000) may be genomic DNA extracted from a sample using conventional techniques, or a cDNA or genomic library produced by conventional techniques, or synthetic DNA, or the like. Treatment (1001) usually entails fragmentation by a conventional technique, such as chemical fragmentation, enzymatic fragmentation, or mechanical fragmentation, followed by denaturation to produce single stranded DNA fragments. Adaptor oligonucleotides (1004), in this example, are used to form (1008) a population (1010) of DNA circles by the method illustrated in FIG. 2A. In one aspect, each member of population (1010) has an adaptor with an identical primer binding site and a DNA fragment from source nucleic acid (1000). The adapter also may have other functional elements including, but not limited to, tagging sequences, attachment sequences, palindromic sequences, restriction sites, functionalization sequences, and the like. In other embodiments, classes of DNA circles may be created by providing adaptors having different primer binding sites. After DNA circles (1010) are formed, a primer and rolling circle replication (RCR) reagents may be added to generate (1011) in a conventional RCR reaction a population (1012) of concatemers (1015) of the complements of the adaptor oligonucleotide and DNA fragments, which population can then be isolated using conventional separation techniques. Alternatively, RCR may be implemented by successive ligation of short oligonucleotides, e.g. 6-mers, from a mixture containing all possible sequences, or if circles are synthetic, a limited mixture of oligonucleotides having selected sequences for circle replication. Concatemers may also be generated by ligation of target DNA in the presence of a bridging template DNA complementary to both beginning and end of the target molecule. A population of different target DNA may be converted in concatemers by a mixture of corresponding bridging templates. Isolated concatemers (1014) are then disposed (1016) onto support surface (1018) to form a random array of single molecules. Attachment may also include wash steps of varying stringencies to remove incompletely attached single molecules or other reagents present from earlier preparation steps whose presence is undesirable or that are nonspecifically bound to surface (1018). Concatemers (1020) can be fixed to surface (1018) by a variety of techniques, including covalent attachment and non-covalent attachment. In one embodiment, surface (1018) may have attached capture oligonucleotides that form complexes, e.g. double stranded duplexes, with a segment of the adaptor oligonucleotide, such as the primer binding site or other elements. In other embodiments, capture oligonucleotides may comprise oligonucleotide clamps, or like structures, that form triplexes with adaptor oligonucleotides, e.g. Gryaznov et al, U.S. Pat. No. 5,473,060. In another embodiment, surface (1018) may have reactive functionalities that react with complementary functionalities on the concatemers to form a covalent linkage, e.g. by way of the same techniques used to attach cDNAs to microarrays, e.g. Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g. several hundred nucleotides or larger, may also be efficiently attached to hydrophobic surfaces, such as a clean glass surface that has a low concentration of various reactive functionalities, such as —OH groups. Concatemers of DNA fragments may be further amplified in situ after disposition of a surface. For example after disposition, concatemer may be cleaved by reconstituting a restriction site in adaptor sequences by hybridization of an oligonucleotide, after which the fragments are circularized as described below and amplified in situ by a RCR reaction.

FIG. 3B illustrates a section (1102) of a surface of a random array of single molecules, such as single stranded polynucleotides. Such molecules under conventional conditions (a conventional DNA buffer, e.g. TE, SSC, SSPE, or the like, at room temperature) form random coils that roughly fill a spherical volume in solution having a diameter of from about 100 to 300 nm, which depends on the size of the DNA and buffer conditions, in a manner well known in the art, e.g. Edvinsson, "On the size and shape of polymers and polymer complexes," Dissertation 696 (University of Uppsala, 2002). One measure of the size of a random coil polymer, such as single stranded DNA, is a root mean square of the end-to-end distance, which is roughly a measure of the diameter of the randomly coiled structure. Such diameter, referred to herein as a "random coil diameter," can be measured by light scatter, using instruments, such as a Zetasizer Nano System (Malvern Instruments, UK), or like instrument. Additional size measures of macromolecular structures of the invention include molecular weight, e.g. in Daltons, and total polymer length, which in the case of a branched polymer is the sum of the lengths of all its branches. Upon attachment to a surface, depending on the attachment chemistry, density of linkages, the nature of the surface, and the like, single stranded polynucleotides fill a flattened spheroidal volume that on average is bounded by a region (1107) defined by dashed circles (1108) having a diameter (1110), which is approximately equivalent to the diameter of a concatemer in random coil configuration. Stated another way, in one aspect, macromolecular structures, e.g. concatemers, and the like, are attached to surface (1102) within a region that is substantially equivalent to a projection of its random coil state onto surface (1102), for example, as illustrated by dashed circles (1108). An area occupied by a macromolecular structure can vary, so that in some embodiments, an expected area may be within the range of from 2-3 times the area of projection (1108) to some fraction of such area, e.g. 25-50 percent. As mentioned elsewhere, preserving the compact form of the macromolecular structure on the surface allows a more intense signal to be produced by probes, e.g. fluorescently labeled oligonucleotides, specifically directed to components of a macromolecular structure or concatemer. The size of diameter (1110) of regions (1107) and distance (1106) to the nearest neighbor region containing a single molecule are two quantities of interest in the fabrication of arrays. A variety of distance metrics may be employed for measuring the closeness of single molecules on a surface, including center-to-center distance of regions (1107), edge-to-edge distance of regions (1007), and the like. Usually, center-to-center distances are employed herein. The selection of these parameters in fabricating arrays of the invention depends in part on the signal generation and detection systems used in the analytical processes. Generally, densities of single molecules are selected that permit at least twenty percent, or at least thirty percent, or at least forty percent, or at least a majority of the molecules to be resolved individually by the signal generation and detection systems used. In one aspect, a density is selected that permits at least seventy percent of the single molecules to be individually resolved. In one aspect, whenever scanning electron microscopy is employed, for example, with molecule-specific probes having gold nanoparticle labels, e.g. Nie et al (2006), Anal. Chem., 78: 1528-1534, which is incorporated by reference, a density is selected such that at least a majority of single molecules have a nearest neighbor distance of 50 nm or greater; and in another aspect, such density is selected to ensure that at least seventy percent of single molecules have a nearest neighbor distance of 100 nm or greater. In another aspect, whenever optical microscopy is employed, for example with molecule-specific probes having fluorescent labels, a density is selected such that at least a majority of single molecules have a nearest neighbor distance of 200 nm or greater; and in another aspect, such density is selected to ensure that at least seventy percent of single molecules have a nearest neighbor distance of 200 nm or greater. In still another aspect, whenever optical microscopy is employed, for example with molecule-specific probes having fluorescent labels, a density is selected such that at least a majority of single molecules have a nearest neighbor distance of 300 nm or greater; and in another aspect, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment, whenever optical microscopy is used, a density is selected such that at least a majority of single molecules have a nearest neighbor distance of at least twice the minimal feature resolution power of the microscope. In another aspect, polymer molecules of the invention are disposed on a surface so that the density of separately detectable polymer molecules is at least 1000 per $\mu m^2$, or at least 10,000 per $\mu m^2$, or at least 100,000 per $\mu m^2$.

In another aspect of the invention, illustrated for a particular embodiment in FIG. 3C, the requirement of selecting densities of randomly disposed single molecules to ensure desired nearest neighbor distances is obviated by providing on a surface discrete spaced apart regions that are substantially the sole sites for attaching single molecules. That is, in such embodiments the regions on the surface between the discrete spaced apart regions, referred to herein as "inter-regional areas," are inert in the sense that concatemers, or other macromolecular structures, do not bind to such regions. In some embodiments, such inter-regional areas may be treated with blocking agents, e.g. DNAs unrelated to concatemer DNA, other polymers, and the like As in FIG. 1A, source nucleic acids (1000) are fragmented and adaptored (1002) for circularization (1010), after which concatemers are formed by RCR (1012). Isolated concatemers (1014) are then applied to surface (1120) that has a regular array of discrete spaced apart regions (1122) that each have a nearest neighbor distance (1124) that is determined by the design and fabrication of surface (1120). As described more fully below, arrays of discrete spaced apart regions (1122) having micron and submicron dimensions for derivatizing with capture oligonucleotides or reactive functionalities can be fabricated using conventional semiconductor fabrication techniques, including electron beam lithography, nano imprint technology, photolithography, and the like. Generally, the area of discrete spaced apart regions (1122) is selected, along with attachment chemistries, macromolecular structures employed, and the like, to correspond to the size of single molecules of the invention so that when single molecules are applied to surface (1120) substantially every region (1122) is occupied by no more than one single molecule. The likelihood of having only one single molecule per discrete spaced apart region may be increased by selecting a density of reactive functionalities or capture oligonucleotides that results in fewer such moieties than their respective complements on single molecules. Thus, a single molecule will "occupy" all linkages to the surface at a particular discrete spaced apart region, thereby reducing the chance that a second single molecule will also bind to the same region. In particular, in one embodiment, substantially all the capture oligonucleotides in a discrete spaced apart region hybridize to adaptor oligonucleotides a single macromolecular structure. In one aspect, a discrete spaced apart region contains a number of reactive functionalities or capture oligonucleotides that is from about ten percent to about fifty percent of the number of complementary functionalities or adaptor oligonucleotides of a single molecule. The length and sequence(s) of capture oligonucleotides may vary widely, and may be selected in accordance with well known principles, e.g. Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). In one aspect, the lengths of capture oligonucleotides are in a range of from 6 to 30 nucleotides, and in another aspect, within a range of from 8 to 30 nucleotides, or from 10 to 24 nucleotides. Lengths and sequences of capture oligonucleotides are selected (i) to provide effective binding of macromolecular structures to a surface, so that losses of macromolecular structures are minimized during steps of analytical operations, such as washing, etc., and (ii) to avoid interference with analytical operations on analyte molecules, particularly when analyte molecules are DNA fragments in a concatemer. In regard to (i), in one aspect, sequences and lengths are selected to provide duplexes between capture oligonucleotides and their complements that are sufficiently stable so that they do not dissociate in a stringent wash. In regard to (ii), if DNA fragments are from a particular species of organism, then databases, when available, may be used to screen potential capture sequences that may form spurious or undesired hybrids with DNA fragments. Other factors in selecting sequences for capture oligonucleotides are similar to those considered in selecting primers, hybridization probes, oligonucleotide tags, and the like, for which there is ample guidance, as evidenced by the references cited below in the Definitions section.

In one aspect, the area of discrete spaced apart regions (1122) is less than 1 $\mu m^2$; and in another aspect, the area of discrete spaced apart regions (1122) is in the range of from 0.04 $\mu m^2$ to 1 $\mu m^2$; and in still another aspect, the area of discrete spaced apart regions (1122) is in the range of from 0.2 $\mu m^2$ to 1 $\mu m^2$. In another aspect, when discrete spaced apart regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of regions (1122) are in the range of from 0.25 $\mu m$ to 20 $\mu m$; and in another aspect, such distances are in the range of from 1 $\mu m$ to 10 $\mu m$, or in the range from 50 to 1000 nm. In one aspect, regions (1120) may be arranged on surface (1018) in virtually any pattern in which regions (1122) have defined locations, i.e. in any regular array, which makes signal collection and data analysis functions more efficient. Such patterns include, but are not limited to, concentric circles of regions (1122), spiral patterns, rectilinear patterns, hexagonal patterns, and the like. Preferably, regions (1122) are arranged in a rectilinear or hexagonal pattern.

Source Nucleic Acids and Circularization of Target Sequences

Figure 1C:
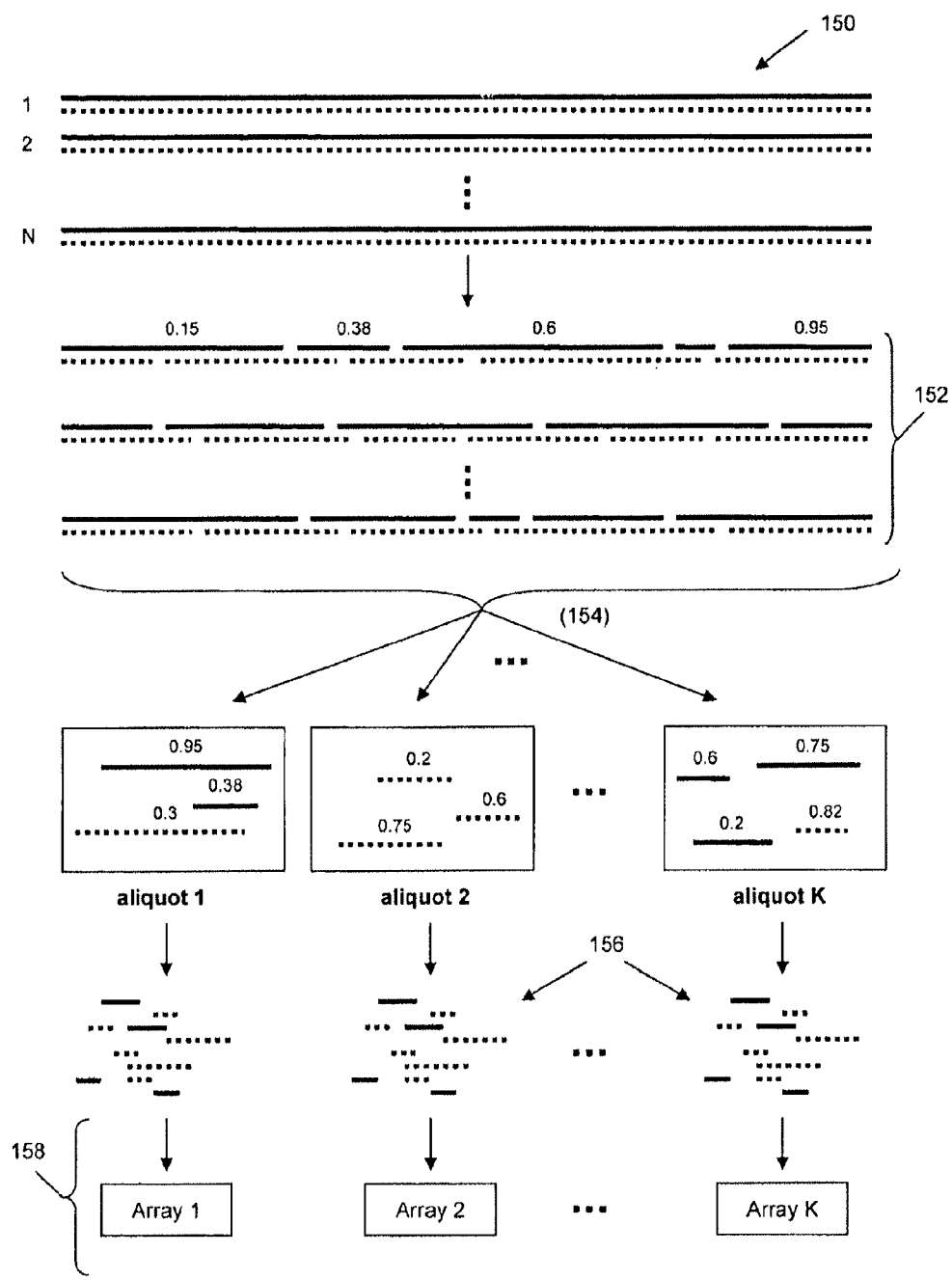

Target polynucleotides for analysis may be extracted or derived from a sample, such as genomic DNA or cDNAs, from a patient, from an environmental sample, or from an organism of economic interest, or the like. As diagrammed in FIG. 1C, random arrays comprising concatemers of DNA fragments from such samples are useful in providing genome-wide analyses, including sequence determination, SNP measurement, allele quantitation, copy number measurements, and the like. For mammalian-sized genomes (150), fragmentation is carried out in at least two stages, a first stage to generate a population (152) of fragments in a size range of from about 100 kilobases (Kb) to about 250 kilobases, and a second stage after aliquoting (154), applied separately to the 100-250 Kb fragments, to generate fragments (156) in the size range of from about 50 to 600 nucleotides, and more preferably in the range of from about 300 to 600 nucleotides, which are then used to generate concatemers for a random array. The amount of genomic DNA required for constructing arrays of the invention can vary widely. In one aspect, for mammalian-sized genomes, fragments are generated from at least 10 genome-equivalents of DNA; and in another aspect, fragments are generated from at least 30 genome-equivalents of DNA; and in another aspect, fragments are generated from at least 60 genome-equivalents of DNA (i.e. 10, 30, or 60 coverage amounts).

Figure 2B:
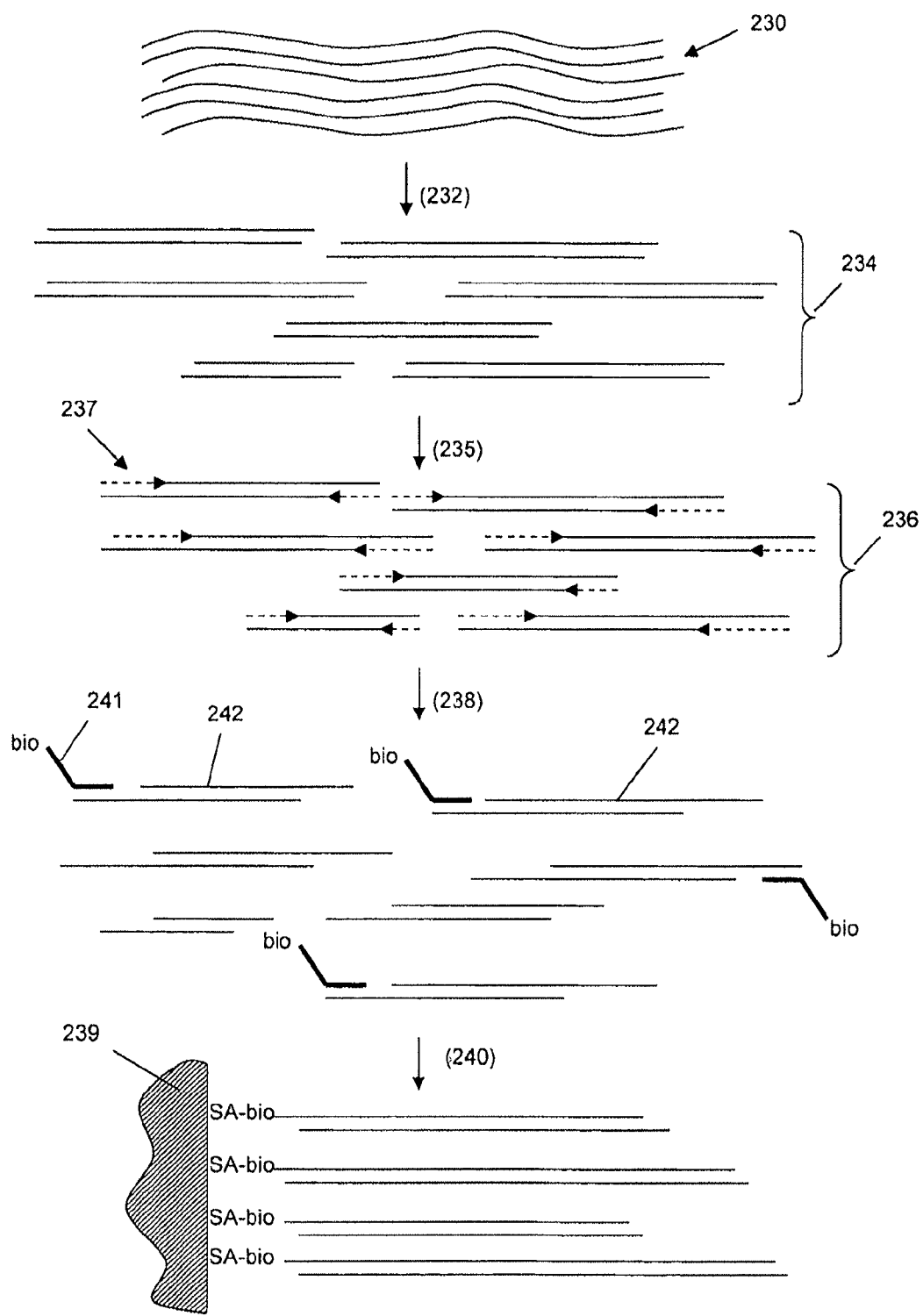

For mammalian-sized genomes, an initial fragmentation of genomic DNA can be achieved by digestion with one or more "rare" cutting restriction endonucleases, such as Not I, Asc I, Bae I, CspC I, Pac I, Fse I, Sap I, Sfi I, Psr I, or the like, to produce fragments that are target polynucleotides for analysis by the invention; that is, such restriction fragments are processed by the random fragmentation techniques described above. Specific fragments may be isolated from such digested DNA for subsequent processing as illustrated in FIG. 2B. Genomic DNA (230) is digested (232) with a rare cutting restriction endonuclease to generate fragments (234), after which the fragments (234) are further digested for a short period (i.e. the reaction is not allowed to run to completion) with a 5' single stranded exonuclease, such as λ exonuclease, to expose sequences (237) adjacent to restriction site sequences at the end of the fragments. Such exposed sequences will be unique for each fragment. Accordingly, biotinylated primers (241) specific for the ends of desired fragments can be annealed to a capture oligonucleotide for isolation; or alternatively, such fragments can be annealed to a primer having a capture moiety, such as biotin, and extended with a DNA polymerase that does not have strand displacement activity, such as Taq polymerase Stoffel fragment. After such extension, the 3' end of primers (241) abut the top strand of fragments (242) such that they can be ligated to form a continuous strand. The latter approach may also be implemented with a DNA polymerase that does have strand displacement activity and replaces the top strand (242) by synthesis. In either approach, the biotinylated fragments may then be isolated (240) using a solid support (239) derivatized with streptavidin.

In another aspect, primer extension from a genomic DNA template is used to generate a linear amplification of selected sequences greater than 10 kilobases surrounding genomic regions of interest. For example, to create a population of defined-sized targets, 20 cycles of linear amplification is performed with a forward primer followed by 20 cycles with a reverse primer. Before applying the second primer, the first primer is removed with a standard column for long DNA purification or degraded if a few uracil bases are incorporated. A greater number of reverse strands are generated relative to forward strands resulting in a population of double stranded molecules and single stranded reverse strands. The reverse primer may be biotinylated for capture to streptavidin beads which can be heated to melt any double stranded homoduplexes from being captured. All attached molecules will be single stranded and representing one strand of the original genomic DNA.

The products produced can be fragmented to 0.2-2 kb in size, or more preferably, 0.3-0.6 kb in size (effectively releasing them from the solid support) and circularized for an RCR reaction. In one method of circularization, illustrated in FIG. 2A, after genomic DNA (200) is fragmented and denatured (202), single stranded DNA fragments (204) are first treated with a terminal transferase (206) to attach a poly dA tails (208) to 3-prime ends. This is then followed by ligation (212) of the free ends intra-molecularly with the aid of bridging oligonucleotide (210). that is complementary to the poly dA tail at one end and complementary to any sequence at the other end by virtue of a segment of degenerate nucleotides. Duplex region (214) of bridging oligonucleotide (210) contains at least a primer binding site for RCR and, in some embodiments, sequences that provide complements to a capture oligonucleotide, which may be the same or different from the primer binding site sequence, or which may overlap the primer binding site sequence. The length of capture oligonucleotides may vary widely, In one aspect, capture oligonucleotides and their complements in a bridging oligonucleotide have lengths in the range of from 10 to 100 nucleotides; and more preferably, in the range of from 10 to 40 nucleotides. In some embodiments, duplex region (214) may contain additional elements, such as an oligonucleotide tag, for example, for identifying the source nucleic acid from which its associated DNA fragment came. That is, in some embodiments, circles or adaptor ligation or concatemers from different source nucleic acids may be prepared separately during which a bridging adaptor containing a unique tag is used, after which they are mixed for concatemer preparation or application to a surface to produce a random array. The associated fragments may be identified on such a random array by hybridizing a labeled tag complement to its corresponding tag sequences in the concatemers, or by sequencing the entire adaptor or the tag region of the adaptor. Circular products (218) may be conveniently isolated by a conventional purification column, digestion of non-circular DNA by one or more appropriate exonucleases, or both.

As mentioned above, DNA fragments of the desired sized range, e.g. 50-600 nucleotides, can also be circularized using circularizing enzymes, such as CircLigase, as single stranded DNA ligase that circularizes single stranded DNA without the need of a template. CircLigase is used in accordance with the manufacterer's instructions (Epicentre, Madison, Wis.). A preferred protocol for forming single stranded DNA circles comprising a DNA fragment and one or more adapters is to use standard ligase such as T4 ligase for ligation an adapter to one end of DNA fragment and than to use CircLigase to close the circle, as described more fully below.

An exemplary protocol for generating a DNA circle comprising an adaptor oligonucleotide and a target sequence using T4 ligase. The target sequence is a synthetic oligo T1N (sequence: 5'-GCATANCACGANGTCAT-NATCGTNCAAACGTCAGTCCANGAATCNAGAT CCACTTAGANTGNCGNNN-3'). The adaptor is made up of 2 separate oligos. The adaptor oligo that joins to the 5' end of T1N is BR2-ad (sequence: 5'-TATCATCTGGATGTTAG-GAAGACAAAAGGAAGCTGAGGACATTAACGGAC-3') and the adaptor oligo that joins to the 3' end of T1N is UR3-ext (sequence: 5'-ACCTTCAGACCAGAT-3') UR3-ext contains a type IIs restriction enzyme site (Acu I: CTTCAG) to provide a way to linearize the DNA circular for insertion of a second adaptor. BR2-ad is annealed to BR2-temp (sequence 5'-NNNNNNNGTCCGTTAATGTC-CTCAG-3') to form a double-stranded adaptor BR2 adaptor. UR3-ext is annealed to biotinylated UR3-temp (sequence 5'-[BIOTIN]ATCTGGTCTGAAGGT-3') to form a double-stranded adaptor UR3 adaptor. 1 pmol of target T1N is ligated to 25 pmol of BR2 adaptor and 10 pmol of UR3 adaptor in a single ligation reaction containing 50 mM Tris-Cl, pH7.8, 10% PEG, 1 mM ATP, 50 mg/L BSA, 10 mM MgCl$_2$, 0.3 unit/µl T4 DNA ligase (Epicentre Biotechnologies, WI) and 10 mM DTT) in a final volume of 10 ul. The ligation reaction is incubated in a temperature cycling program of 15° C. for 11 min, 37° C. for 1 min repeated 18 times. The reaction is terminated by heating at 70° C. for 10 min. Excess BR2 adaptors are removed by capturing the ligated products with streptavidin magnetic beads (New England Biolabs, MA). 3.3 ul of 4× binding buffer (2M NaCl, 80 mM Tris HCl pH7.5) is added to the ligation reaction which is then combined with 15 µg of streptavidin magnetic beads in 1× binding buffer (0.5M NaCl, 20 mM Tris HCl pH7.5). After 15 min incubation in room temperature, the beads are washed twice with 4 volumes of low salt buffer (0.15M NaCl, 20 mM Tris HCl pH7.5). Elution buffer (10 mM Tris HCl pH7.5) is pre-warmed to 70 deg, 10 µl of which is added to the beads at 70° C. for 5 min. After magnetic separation, the supernatant is retained as primary purified sample. This sample is further purified by removing the excess UR3 adaptors with magnetic beads pre-bound with a biotinylated oligo BR-rc-bio (sequence: 5'-[BIOTIN] CTTTTGTCTTCCTAACATCC-3') that is reverse complementary to BR2-ad similarly as described above. The concentration of the adaptor-target ligated product in the final purified sample is estimated by urea polyacrylamide gel electrophoresis analysis. The circularization is carried out by phosphorylating the ligation products using 0.2 unit/µl T4 polynucleotide kinase (Epicentre Biotechnologies) in 1 mM ATP and standard buffer provided by the supplier, and circularized with ten-fold molar excess of a splint oligo UR3-closing-88 (sequence 5'-AGATGATAATCTGGTC-3') using 0.3 unit/µl of T4 DNA ligase (Epicentre Biotechnologies) and 1 mM ATP. The circularized product is validated by performing RCR reactions as described below.

Guidance for selecting conditions and reagents for RCR reactions is available in many references available to those of ordinary skill, as evidence by the following that are incorporated by reference: Kool, U.S. Pat. No. 5,426,180; Lizardi, U.S. Pat. Nos. 5,854,033 and 6,143,495; Landegren, U.S. Pat. No. 5,871,921; and the like. Generally, RCR reaction components comprise single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circles and be extended by the DNA polymerase to form concatemers of DNA circle complements. An exemplary RCR reaction protocol is as follows: In a 50 µL reaction mixture, the following ingredients are assembled: 2-50 pmol circular DNA, 0.5 units/µL phage φ29 DNA polymerase, 0.2 µg/mL BSA, 3 mM dNTP, 1×φ29 DNA polymerase reaction buffer (Amersham). The RCR reaction is carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

Preferably, concatemers produced by RCR are approximately uniform in size; accordingly, in some embodiments, methods of making arrays of the invention may include a step of size-selecting concatemers. For example, in one aspect, concatemers are selected that as a population have a coefficient of variation in molecular weight of less than about 30%; and in another embodiment, less than about 20%. In one aspect, size uniformity is further improved by adding low concentrations of chain terminators, such ddNTPs, to the RCR reaction mixture to reduce the presence of very large concatemers, e.g. produced by DNA circles that are synthesized at a higher rate by polymerases. In one embodiment, concentrations of ddNTPs are used that result in an expected concatemer size in the range of from 50-250 Kb, or in the range of from 50-100 Kb. In another aspect, concatemers may be enriched for a particular size range using a conventional separation techniques, e.g. size-exclusion chromatography, membrane filtration, or the like.

Solid Phase Surfaces for Constructing Random Arrays

A wide variety of supports may be used with the invention. In one aspect, supports are rigid solids that have a surface, preferably a substantially planar surface so that single molecules to be interrogated are in the same plane. The latter feature permits efficient signal collection by detection optics, for example. In another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like. In one aspect, the area of a planar surface may be in the range of from 0.5 to 4 cm$^2$. In one aspect, the solid support is glass or quartz, such as a microscope slide, having a surface that is uniformly silanized. This may be accomplished using conventional protocols, e.g. acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g. Beattie et a (1995), Molecular Biotechnology, 4: 213. Such a surface is readily treated to permit end-attachment of capture oligonucleotides, e.g. by providing capture oligonucleotides with a 3' or 5' triethylene glycol phosphoryl spacer (see Beattie et al, cited above) prior to application to the surface. Many other protocols may be used for adding reactive functionalites to glass and other surfaces, as evidenced by the disclosure in Beaucage (cited above).

Whenever enzymatic processing is not required, capture oligonucleotides may comprise non-natural nucleosidic units and/or linkages that confer favorable properties, such as increased duplex stability; such compounds include, but not limited to, peptide nucleic acids (PNAs), locked nucleic acids (LNA), oligonucleotide N3'→P5' phosphoramidates, oligo-2'-O-alkylribonucleotides, and the like.

In embodiments of the invention in which patterns of discrete spaced apart regions are required, photolithography, electron beam lithography, nano imprint lithography, and nano printing may be used to generate such patterns on a wide variety of surfaces, e.g. Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference.

In one aspect, surfaces containing a plurality of discrete spaced apart regions are fabricated by photolithography. A commercially available, optically flat, quartz substrate is spin coated with a 100-500 nm thick layer of photo-resist. The photo-resist is then baked on to the quartz substrate. An image of a reticle with a pattern of regions to be activated is projected onto the surface of the photo-resist, using a stepper. After exposure, the photo-resist is developed, removing the areas of the projected pattern which were exposed to the UV source. This is accomplished by plasma etching, a dry developing technique capable of producing very fine detail. The substrate is then baked to strengthen the remaining photo-resist. After baking, the quartz wafer is ready for functionalization. The wafer is then subjected to vapor-deposition of 3-aminopropyldimethylethoxysilane. The density of the amino functionalized monomer can be tightly controlled by varying the concentration of the monomer and the time of exposure of the substrate. Only areas of quartz exposed by the plasma etching process may react with and capture the monomer. The substrate is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N—N-dimethylformamide. The substrate is then capable of reacting with amine-modified oligonucleotides. Alternatively, oligonucleotides can be prepared with a 5'-carboxy-modifier-c10 linker (Glen Research). This technique allows the oligonucleotide to be attached directly to the amine modified support, thereby avoiding additional functionalization steps.

In another aspect, surfaces containing a plurality of discrete spaced apart regions are fabricated by nano-imprint lithography (NIL). For DNA array production, a quartz substrate is spin coated with a layer of resist, commonly called the transfer layer. A second type of resist is then applied over the transfer layer, commonly called the imprint layer. The master imprint tool then makes an impression on the imprint layer. The overall thickness of the imprint layer is then reduced by plasma etching until the low areas of the imprint reach the transfer layer. Because the transfer layer is harder to remove than the imprint layer, it remains largely untouched. The imprint and transfer layers are then hardened by heating. The substrate is then put into a plasma etcher until the low areas of the imprint reach the quartz. The substrate is then derivatized by vapor deposition as described above.

In another aspect, surfaces containing a plurality of discrete spaced apart regions are fabricated by nano printing. This process uses photo, imprint, or e-beam lithography to create a master mold, which is a negative image of the features required on the print head. Print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. Random array substrates are manufactured using nano-printing by depositing a pattern of amine modified oligonucleotides onto a homogenously derivatized surface. These oligonucleotides would serve as capture probes for the RCR products. One potential advantage to nano-printing is the ability to print interleaved patterns of different capture probes onto the random array support. This would be accomplished by successive printing with multiple print heads, each head having a differing pattern, and all patterns fitting together to form the final structured support pattern. Such methods allow for some positional encoding of DNA elements within the random array. For example, control concatemers containing a specific sequence can be bound at regular intervals throughout a random array.

Detection Instrumentation

As mentioned above, signals from single molecules on random arrays made in accordance with the invention are generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, $2^{nd}$ Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683. In one aspect, instruments for use with arrays of the invention comprise three basic components: (i) a fluidics system for storing and transferring detection and processing reagents, e.g. probes, wash solutions, and the like, to an array; (ii) a reaction chamber, or flow cell, holding or comprising an array and having flow-through and temperature control capability; and (iii) an illumination and detection system. In one embodiment, a flow cell has a temperature control subsystem with ability to maintain temperature in the range from about 5-95° C., or more specifically 10-85° C., and can change temperature with a rate of about 0.5-2° C. per second. An exemplary detection and imaging systems comprises a 100× objective using TIRF or epi illumination and a 1.3 mega pixel Hamamatsu orca-er-ag on a Zeiss axiovert 200, or like system.

Sequence Analysis of Random Arrays of Target Sequence Concatemers

As mentioned above, random arrays of biomolecules, such as genomic DNA fragments or cDNA fragments, provides a platform for large scale sequence determination and for genome-wide measurements based on counting sequence tags, in a manner similar to measurements made by serial analysis of gene expression (SAGE) or massively parallel signature sequencing, e.g. Velculescu, et al, (1995), Science 270, 484-487; and Brenner et al (2000), Nature Biotechnology, 18: 630-634. Such genome-wide measurements include, but are not limited to, determination of polymorphisms, including nucleotide substitutions, deletions, and insertions, inversions, and the like, determination of methylation patterns, copy number patterns, and the like.

A variety of sequencing methodologies can be used with random arrays of the invention, including, but not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g. Nyren et al, U.S. Pat. No. 6,210,891; Ronaghi, U.S. Pat. No. 6,828,100; Ronaghi et al (1998), Science, 281: 363-365; Balasubramanian, U.S. Pat. No. 6,833,246; Quake, U.S. Pat. No. 6,911,345; Li et al, Proc. Natl. Acad. Sci., 100: 414-419 (2003), which are incorporated by reference, and ligation-based methods, e.g. Shendure et al (2005), Science, 309: 1728-1739, which is incorporated by reference.

In one aspect, parallel sequencing of polynucleotide analytes of concatemers on a random array is accomplished by combinatorial SBH (cSBH), as disclosed by Drmanac in the above-cited patents. In one aspect, a first and second sets of oligonucleotide probes are provide, wherein each sets has member probes that comprise oligonucleotides having every possible sequence for the defined length of probes in the set. For example, if a set contains probes of length six, then it contains 4096 (=$4^6$) probes. In another aspect, first and second sets of oligonucleotide probes comprise probes having selected nucleotide sequences designed to detect selected sets of target polynucleotides. Sequences are determined by hybridizing one probe or pool of probe, hybridizing a second probe or a second pool of probes, ligating probes that form perfectly matched duplexes on their target sequences, identifying those probes that are ligated to obtain sequence information about the target sequence, repeating the steps until all the probes or pools of probes have been hybridized, and determining the nucleotide sequence of the target from the sequence information accumulated during the hybridization and identification steps.

For sequencing operation, in some embodiments, the sets may be divided into subsets that are used together in pools, as disclosed in U.S. Pat. No. 6,864,052, which is incorporated by reference. Probes from the first and second sets may be hybridized to target sequences either together or in sequence, either as entire sets or as subsets, or pools. In one aspect, lengths of the probes in the first or second sets are in the range of from 5 to 10 nucleotides, and in another aspect, in the range of from 5 to 7 nucleotides, so that when ligated they form ligation products with a length in the range of from 10 to 20, and from 10 to 14, respectively.

Kits of the Invention

In the commercialization of the methods described herein, certain kits for DNA fragmentation, aliqoting, amplification, construction of random arrays, and for using the same for various applications are particularly useful. Kits for applications of random arrays of the invention include, but are not limited to, kits for determining the nucleotide sequence of a target polynucleotide, kits for large-scale identification of differences between reference DNA sequences and test DNA sequences, kits for profiling exons, and the like. A kit typically comprises at least one support having a surface and one or more reagents necessary or useful for constructing a random array of the invention or for carrying out an application therewith. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In one aspect, kits of the invention for carrying out multiple levels of random fragmentation and aliquoting comprise the following components: (a) mechanical appliance and/or one or more nucleases for generating random fragments from one or more target polynucleotides, (b) amplification reagents for replicating random fragments, and (c) vessels for holding aliquots of random fragments. In one embodiment, such vessels are selected from 96-well plates, 384-well plates, or 1536-well plates. In another aspect, the enzyme is DNAse I. In yet another embodiment, the mechanical appliance is an ultrasonic generator.

Analysis of cDNAs

A human cell contains about 300,000 mRNA molecules with average size about 3 kb, e.g. about one Gb or 16% of the size of all chromosomal DNA in the cell. These mRNAs usually represent on the order of about 10,000 different genes. Usually about 50% of all mRNA molecules are generated from about a few hundred highly expressed genes. Large majority of the expressed genes in a cell are represented with 1-30 mRNA molecules. Full length or long cDNA may be prepared fusing mRNA templates. Various normalization or cleaning methods may be used to remove majority of highly redundant mRNA molecules. Furthermore it is found that at least 50% of genes has on average three splice variants. For complete gene expression analysis there is a need to determine complete or almost complete sequences of all different mRNA/cDNA present in the cell. Such analysis will give full characterization of the expressed splice variants and protein haplotypes including expression level of each variant. A variant of aliquoting process provides ability to obtain this complete analysis of expressed gene sequences.

For most of the genes that have 1-30 mRNA molecules per cell dilution and or direct aliquoting of full length or very long cDNA would be adjusted similarly to analysis of 15× coverage of diploid chromosomal DNA. About 96-384 or up to 1536 aliquots assures that 30 or even 100 cDNA molecules transcribed from the same gene in most case will be placed in separate aliquots. Only rarely a aliquot will have two cDNA representing the same gene. The number of aliquots may be increased that most of the distinct mRNA variants are represented at least two times in the set of the aliquots or at least 10-20 times for the purpose of accurate determination of expression level of each variant. At the same time highly expressed genes with several hundreds or a few thousands of cDNAs, if they are not removed, would have multiple cDNA representatives per aliquot. For these genes a special set of 96 or 384 or more low complexity aliquots may be prepared by using about 10-100 fold less cDNA per aliquot.

cDNA in the aliquots may be protected by various carriers such as tRNA or glycogen. cDNA will be replicated 10-1000 fold as full length or in multiple segments covering the entire cDNA. The obtained DNA may be further fragmented to second-sized fragments that are appropriate for the method of choice for sequence analysis. In the preferred method second sized fragments are tagged with an oligonucleotide of known sequence. A different oligo with one or more base differences is used for each aliquot. After tagging DNA from some or all aliquots is mixed to simplify further preparation for sequencing. Sequencing may be done with various methods as described for chromosomal DNA. In the preferred mode 5-10 fold sequence coverage is obtained for each cDNA in each aliquot, but as low as 1-2 fold coverage may be used. After sequencing, short reads coming from the same aliquot may be assembled to form full length sequences of each of cDNA molecules present in the aliquot.

Because in most cases a gene is represented with only one cDNA molecule per aliquot the actual sequence of that molecule is obtained reveling actual protein haplotype or splice variant that would be synthesized from that mRNA molecule. This is equivalent to full length sequencing of individual full-length cDNA clones. By comparing sequence reads or assembled cDNA sequences across aliquots all identical variants may be counted and the number of occurrence indicate expression level for each mRNA variant.

Traditional methods of cloning have several drawbacks including the propensity of bacteria to exclude sequences from plasmid replication and the time consuming and reagent-intensive protocols required to generate clones of individual cDNA molecules. We have previously demonstrated the ability to create linear single-stranded amplifications of DNA molecules that have been closed into a circular form. These large concatemeric, linear forms arise from a single molecule and can act as efficient, isolated targets for PCR when separated into a single reaction chamber, in much the same way a bacterial colony is picked to retrieve the cDNA containing plasmid. We plan to develop this approach as a means to select cDNA clones without having to pass through a cell-based clonal selection step.

The first step of this procedure will involve ligating a gene specific oligonucleotide directed to the 5-prime end with a poly dA sequence for binding to the poly dT sequence of the 3-prime end of the cDNA. This oligonucleotide acts as a bridge to allow T4 DNA ligase to ligate the two ends and form a circle.

The second step of the reaction is to use a primer, or the bridging oligonucleotide, for a strand displacing polymerase such as Phi 29 polymerase to create a concatemer of the circle. The long linear molecules will then be diluted and arrayed in 1536 well plates such that wells with single molecules can be selected. To ensure about 10% of the wells contain 1 molecule approximately 90% would have to be sacrificed as having no molecules. To detect the wells that are positive we plan to hybridize a dendrimer that recognizes a universal sequence in the target to generate 10K-100K dye molecules per molecule of target. Excess dendrimer could be removed through hybridization to biotinylated capture oligos. The wells will be analyzed with a fluorescent plate reader and the presence of DNA scored. Positive wells will then be re-arrayed to consolidate the clones into plates with complete wells for further amplification Splice Variant Detection and Exon Profiling The process described is based on random DNA arrays and "smart" probe pools for the identification and quantification of expression levels of thousands of genes and their splice variants. In eukaryotes, as the primary transcript emerges from the transcription complex, spliceosomes interact with splice sites on the primary transcript to excise out the introns, e.g. Maniatis et al, Nature, 418: 236-243 (2002). However, because of either mutations that alter the splice site sequences, or external factors that affect spliceosome interaction with splice sites, alternative splice sites, or cryptic splice sites, could be selected resulting in expression of protein variants encoded by mRNA with different sets of exons. Surveys of cDNA sequences from large scale EST sequencing projects indicated that over 50% of the genes have known splice variants. In a recent study using a microarray-based approach, it was estimated that as high as 75% of genes are alternatively spliced, e.g. Johnson et al, Science, 302: 2141-2144 (2003).

The diversity of proteins generated through alternative splicing could partially contribute to the complexity of biological processes in higher eukaryotes. This also leads to the implication that the aberrant expression of variant protein forms could be responsible for pathogenesis of diseases. Indeed, alternative splicing has been found to associate with various diseases like growth hormone deficiency, Parkinson's disease, cystic fibrosis and myotonic dystrophy, e.g. Garcia-Blanco et al, Nature Biotechnology, 22: 535-546 (2004). Because of the difficulty in isolating and characterizing novel splice variants, the evidence implicating roles of splice variants in cancer could represent the tip of the iceberg. With the availability of tools that could rapidly and reliably characterize splicing patterns of mRNA, it would help to elucidate the role of alternative splicing in cancer and in disease development in general.

In one aspect, methods of the invention permit large-scale measurement of splice variants with the following steps: (a) Prepare full length first strand cDNA for targeted or all mRNAs. (b) Circularize the generated full length (or all) first strand cDNA molecules by incorporating an adapter sequence. (c) By using primer complementary to the adapter sequence perform rolling circle replication (RCR) of cDNA circles to form concatemers with over 100 copies of initial cDNA. (d) Prepare random arrays by attaching RCR produced "cDNA balls" to glass surface coated with capture oligonucleotide complementary to a portion of the adapter sequence; with an advanced submicron patterned surface one $mm^2$ can have between 1-10 million cDNA spots; note that the attachment is a molecular process and does not require robotic spotting of individual "cDNA balls" or concatemers. (e) Starting from pre-made universal libraries of 4096 6-mers and 1024 labeled 5-mers, use a sophisticated computer program and a simple robotic pipettor to create 40-80 pools of about 200 6-mers and 20 5-mers for testing all 10,000 or more exons in targeted 1000 or more up to all known genes in the sample organism/tissue. (f) In a 4-8 hour process, hybridize/ligate all probe pools in 40-80 cycles on the same random array using an automated microscope-like instrument with a sensitive 10-mega pixel CCD detector for generating an array image for each cycle. (g) Use a computer program to perform spot signal intensity analysis to identify which cDNA is on which spot, and if any of the expected exons is missing in any of the analyzed genes. Obtain exact expression levels for each splice variant by counting occurrences in the array.

This system provides a complete analysis of the exon pattern on a single transcript, instead of merely providing information on the ratios of exon usage or quantification of splicing events over the entire population of transcribed genes using the current expression arrays hybridized with labeled mRNA/cDNA. At the maximum limit of its sensitivity, it allows a detailed analysis down to a single molecule of a mRNA type present in only one in hundreds of other cells; this would provide unique potentials for early diagnosis of cancer cells. The combination of selective cDNA preparation with an "array of random arrays" in a standard 384-well format and with "smart" pools of universal short probes provides great flexibility in designing assays; for examples, deep analysis of a small number of genes in selected samples, or more general analysis in a larger number of samples, or analysis of a large number of genes in smaller number of samples. The analysis provides simultaneously 1) detection of each specific splice variant, 2) quantification of expression of wild type and alternatively spliced mRNAs. It can also be used to monitor gross chromosomal alterations based on the detection of gene deletions and gene translocations by loss of heterozygosity and presence of two sub-sets of exons from two genes in the same transcript on a single spot on the random array. The exceptional capacity and informativeness of this assay is coupled with simple sample preparation from very small quantities of mRNA, fully-automated assay based on all pre-made, validated reagents including libraries of universal labeled and unlabeled probes and primers/adapters that will be ultimately developed for all human and model organism genes. The proposed splice variant profiling process is equivalent to high throughput sequencing of individual full length cDNA clones; rSBH throughput can reach one billion cDNA molecules profiled in a 4-8 hour assay. This system will provide a powerful tool to monitor changes in expression levels of various splice variants during disease emergence and progression. It can enable discovery of novel splice variants or validate known splice variants to serve as biomarkers to monitor cancer progression. It can also provide means to further understanding the roles of alternative splice variants and their possible uses as therapeutic targets. Universal nature and flexibility of this low cost and high throughput assay provides great commercial opportunities for cancer research and diagnostics and in all other biomedical areas. This high capacity system is ideal for service providing labs or companies.

Preparation of templates for in vitro transcription. Exon sequences are cloned into the multiple cloning sites (MCS) of plasmid pBluescript, or like vector. For the purposes of demonstrating the usefulness of the probe pools, it is not necessary to clone the contiguous full-length sequence, nor to maintain the proper protein coding frame. For genes that are shorter than 1 kb, PCR products are generated from cDNA using gene specific oligos for the full length sequence. For longer genes, PCR products are generated comprising about 500 bp that corresponding to contiguous block of exons and ordered the fragments by cloning into appropriate cloning sites in the MCS of pBluescript. This is also the approach for cloning the alternative spliced versions, since the desired variant might not be present in the cDNA source used for PCR.

The last site of the MCS is used to insert a string of 40 A's to simulate the polyA tails of cellular mRNA. This is to control for the possibility that the polyA tail might interfere with the sample preparation step described below, although it is not expected to be a problem since a poly-dA tail is incorporated in sample preparation of genomic fragments as described. T7 RNA polymerase will be used to generate the run-off transcripts and the RNA generated will be purified with the standard methods.

Preparation of samples for arraying. Because the probe pools are designed for specific genes, cDNA is prepared for those specific genes only. For priming the reverse transcription reactions, gene-specific primers are used, therefore for 1000 genes, 1000 primers are used. The location of the priming site for the reverse transcription is selected with care, since it is not reasonable to expect the synthesis of cDNA>2 kb to be of high efficiency. It is quite common that the last exon would consist of the end of the coding sequence and a long 3' untranslated region. In the case of CD44 for example, although the full-length mRNA is about 5.7 kb, the 3' UTR comprises of 3 kb, while the coding region is only 2.2 kb. Therefore the logical location of the reverse transcription primer site is usually immediately downstream of the end of the coding sequence. For some splice variants, the alternative exons are often clustered together as a block to create a region of variability. In the case of Tenascin C variants (8.5 kb), the most common isoform has a block of 8 extra exons, and there is evidence to suggest that there is variability in exon usage in that region. So for Tenascin C, the primer will be located just downstream of that region. Because of the concern of synthesizing cDNA with length>2 kb, for long genes, it might be necessary to divide the exons into blocks of 2 kb with multiple primers.

Reverse transcription reactions may be carried out with commercial systems, e.g. SuperScript III system from Invitrogen (Carlsbad, Calif.) and the StrataScript system from Stratagene (La Jolla, Calif.). Once single stranded cDNA molecules are produced, the rest of the procedures involved putting on the adaptor sequence, circularization of the molecule and RCR as described above. The 5' ends of the cDNAs are basically the incorporated gene-specific primers used for initiating the reverse transcription. By incorporating a 7 base universal tag on the 5' end of the reverse-transcription priming oligos, all the cDNA generated will carry the same 7 base sequence at the 5' end. Thus a single template oligonucleotide that is complementary to both the adaptor sequence and the universal tag can be used to ligate the adaptor to all the target molecules, without using the template oligonucleotide with degenerate bases. As for the 3' end of the cDNA (5' end of the mRNA) which is usually ill-defined, it may be treated like a random sequence end of a genomic fragment. Similar methods of adding a polyA tail will be applied, thus the same circle closing reaction may also be used.

Reverse transcriptases are prone to terminate prematurely to create truncated cDNAs. Severely truncated cDNAs probably will not have enough probe binding sites to be identified with a gene assignment, thus would not be analyzed. cDNA molecules that are close, but not quite full-length, may show up as splice variant with missing 5' exons. If there are no corroborating evidence from a sequence database to support such variants, they may be discounted. A way to avoid such problem is to select for only the full-length cDNA (or those with the desired 3' end) to be compatible with circle closing reaction, then any truncated molecules will not be circularized nor replicated. First a dideoxy-cytosine residue can be added to the 3' end of all the cDNA to block ligation, then by using a mismatch oligo targeting the desired sequence, a new 3' end can be generated by enzyme mismatch cleavage using T4 endonuclease VII. With the new 3' end, the cDNA can proceed with the adding a poly-dA tail and with the standard protocols of circularization and replication.

Replicated and arrayed concatemers of the exon fragments may be carried out using combinatorial SBH, as described above. The algorithm of the following steps may be used to select 5-mer and 6-mer probes for use in the technique:

Step 1: Select 1000-2000 shortest exons (total about 20-50 kb), and find out matching sequences for each of 1024 available labeled 5-mers. On average each 5-mer will occur 20 times over 20 kb, but some may occur over 50 or over 100 times. By selecting the most frequent 5-mer, the largest number of short exons will be detected with the single labeled probe. A goal would be to detect about 50-100 short exons (10%-20% of 500 exons) per cycle. Thus less than 10 labeled probes and 50-100 unlabeled 6-mers would be sufficient. Small number of labeled probes is favorable because it minimizes overall fluorescent background.

Step 2. Find out all 6-mers that are contiguous with all sites in all 1000 genes that are complementary to 10 selected 5-mers. On average 20 such sites will exist in each 2 kb gene. Total number of sites would be about 20,000, e.g., each 6-mer on average will occur 5 times. Sort 6-mers by the hit frequency. The most frequent may have over 20 hits, e.g.

such 6-mer will detect 20 genes through combinations with 10 labeled probes. Thus, to get a single probe pair for each of the 500 genes a minimum of 25 6-mer probes would be required. Realistically, 100 to 200 6-mers may be required.

Due to benefits of combinatorial SBH that uses pre-made libraries of 6-mer and 5-mer probes 40 probe pools are readily prepared with about 200 probes per pool using established pipetting robotics. The information generated is equivalent to having over 3 probes per exon, therefore the use of 8000 5-mers and 6-mers effectively replaces the 30,000 longer exons specific probes required for a single set of 1000 genes.

Exon profiling. The profiling of exons can be performed in two phases: the gene identification phase and the exon identification phase. In the gene identification phase, each concatemer on the array can be uniquely identified with a particular gene. In theory, 10 probe pools or hybridization cycles will be enough to identify 1000 genes using the following scheme. Each gene is assigned a unique binary code. The number of binary digits thus depends on the total number of genes: 3 digits for 8 genes, 10 digits for 1024 genes. Each probe pool is designed to correspond to a digit of the binary code and would contain probes that would hit a unique combination of half of the genes and one hit per gene only. Thus for each hybridization cycle, an unique half of the genes will score a 1 for that digit and the other half will score zero. Ten hybridization cycles with 10 probe pools will generate 1024 unique binary codes, enough to assign 1000 unique genes to all the concatemers on the array. To provide redundancy in the identification data, 15-20 cycles would be used. If 20 cycles are used, it would provide 1 million unique binary codes and there should be enough information to account for loss of signals due to missing exons or gene deletions. It will also be equivalent to having 10 data points per gene (20 cycles of 500 data point each give 10,000 data points total), or one positive probe-pair per exon, on average. At this point after 20 cycles, this system is capable of making assignment of 1 million unique gene identities to the ampliots. Therefore by counting gene identities of the ampliots, one can determine quantitatively the expression level of all the genes (but not sub-typing of splice variants) in any given samples.

After identifying each ampliot with a gene assignment, its exon pattern will be profiled in the exon identification phase. For the exon identification phase, one exon per gene in all or most of the genes is tested per hybridization cycle. In most cases 10-20 exon identification cycles should be sufficient. Thus, in the case of using 20 exon identification cycles we will obtain information of 2 probes per each of 10 exons in each gene. For genes with more than 20 exons, methods can be developed so that 2 exons per gene can be probed at the same cycle. One possibility is using multiple fluorophores of different colors, and another possibility is to exploit differential hybrid stabilities of different ligation probe pairs.

In conclusion, a total of about 40 assay cycles will provide sufficient information to obtain gene identity at each spot and to provide three matching probe-pairs for each of 10,000 exons with enough informational redundancy to provide accurate identification of missing exons due to alternative splicing or chromosomal deletions.

Definitions

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Complementary or substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

"Genetic locus," or "locus" in reference to a genome or target polynucleotide, means a contiguous subregion or segment of the genome or target polynucleotide. As used herein, genetic locus, or locus, may refer to the position of a nucleotide, a gene, or a portion of a gene in a genome, including mitochondrial DNA, or it may refer to any contiguous portion of genomic sequence whether or not it is within, or associated with, a gene. In one aspect, a genetic locus refers to any portion of genomic sequence, including mitochondrial DNA, from a single nucleotide to a segment of few hundred nucleotides, e.g. 100-300, in length.

"Genetic variant" means a substitution, inversion, insertion, or deletion of one or more nucleotides at genetic locus, or a translocation of DNA from one genetic locus to another genetic locus. In one aspect, genetic variant means an alternative nucleotide sequence at a genetic locus that may be present in a population of individuals and that includes nucleotide substitutions, insertions, and deletions with respect to other members of the population. In another aspect, insertions or deletions at a genetic locus comprises the addition or the absence of from 1 to 10 nucleotides at such locus, in comparison with the same locus in another individual of a population.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1M, more usually less than about 500 mM and less than about 200 mM. A "hybridization buffer" is a buffered salt solution such as 5×SSPE, or the like. Hybridization temperatures can be as low as 5° C., but are typically greater than 22° C., more typically greater than about 30° C., and preferably in excess of about 37° C. Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A laboratory Manual" $2^{nd}$ Ed. Cold Spring Harbor Press (1989) and Anderson "Nucleic Acid Hybridization" $1^{st}$ Ed., BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213. Enzymatic ligation usually takes place in a ligase buffer, which is a buffered salt solution containing any required divalent cations, cofactors, and the like, for the particular ligase employed.

"Microarray" or "array" refers to a solid phase support having a surface, usually planar or substantially planar, which carries an array of sites containing nucleic acids, such that each member site of the array comprises identical copies of immobilized oligonucleotides or polynucleotides and is spatially defined and not overlapping with other member sites of the array; that is, the sites are spatially discrete. In some cases, sites of a microarray may also be spaced apart as well as discrete; that is, different sites do not share boundaries, but are separated by inter-site regions, usually free of bound nucleic acids. Spatially defined hybridization sites may additionally be "addressable" in that its location and the identity of its immobilized oligonucleotide are known or predetermined, for example, prior to its use. In some aspects, the oligonucleotides or polynucleotides are single stranded and are covalently attached to the solid phase support, usually by a 5'-end or a 3'-end. In other aspects, oligonucleotides or polynucleotides are attached to the solid phase support non-covalently, e.g. by a biotin-streptavidin linkage, hybridization to a capture oligonucleotide that is covalently bound, and the like. Conventional microarray technology is reviewed in the following references: Schena, Editor, Microarrays: A Practical Approach (IRL Press, Oxford, 2000); Southern, Current Opin. Chem. Biol., 2: 404-410 (1998); Nature Genetics Supplement, 21: 1-60

(1999). As used herein, "random array" or "random microarray" refers to a microarray whose spatially discrete regions of oligonucleotides or polynucleotides are not spatially addressed. That is, the identity of the attached oligonucleoties or polynucleotides is not discernable, at least initially, from its location, but may be determined by a particular operation on the array, e.g. sequencing, hybridizing decoding probes, or the like. Random microarrays are frequently formed from a planar array of microbeads, e.g. Brenner et al, Nature Biotechnology, 18: 630-634 (2000); Tulley et al, U.S. Pat. No. 6,133,043; Stuelpnagel et al, U.S. Pat. No. 6,396,995; Chee et al, U.S. Pat. No. 6,544,732; and the like.

"Mismatch" means a base pair between any two of the bases A, T (or U for RNA), G, and C other than the Watson-Crick base pairs G-C and A-T. The eight possible mismatches are A-A, T-T, G-G, C-C, T-G, C-A, T-C, and A-G.

"Mutation" and "polymorphism" are usually used somewhat interchangeably to mean a DNA molecule, such as a gene, which differs in nucleotide sequence from a reference DNA sequence, or wild type sequence, or normal tissue sequence, by one or more bases, insertions, and/or deletions. In some contexts, the usage of Cotton (Mutation Detection, Oxford University Press, Oxford, 1997) is followed in that a mutation is understood to be any base change whether pathological to an organism or not, whereas a polymorphism is usually understood to be a base change with no direct pathological consequences.

"Nucleoside" as used herein includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide phosphoramidates (referred to herein as "amidates"), peptide nucleic acids (referred to herein as "PNAs"), oligo-2'-β-alkylribonucleotides, polynucleotides containing C-5 propynylpyrimidines, locked nucleic acids (LNAs), and like compounds. Such oligonucleotides are either available commercially or may be synthesized using methods described in the literature.

"Oligonucleotide tag" means an oligonucleotide that is attached to a polynucleotide and is used to identify and/or track the polynucleotide in a reaction. Usually, a oligonucleotide tag is attached to the 3'- or 5'-end of a polynucleotide to form a linear conjugate, sometime referred to herein as a "tagged polynucleotide," or equivalently, an "oligonucleotide tag-polynucleotide conjugate," or "tag-polynucleotide conjugate." Oligonucleotide tags may vary widely in size and compositions; the following references provide guidance for selecting sets of oligonucleotide tags appropriate for particular embodiments: Brenner, U.S. Pat. No. 5,635,400; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths of oligonucleotide tags can vary widely, and the selection of a particular lengths depend on several factors including, without limitation, whether the oligonucleotide tags are employed primarily in hybridization reactions or primarily in enzymatic reactions, whether they are labeled, whether such labeling is direct or indirect, the number of distinguishable oligonucleotide tags required, and the like. In one aspect, oligonucleotide tags can each have a length within a range of from 2 to 36 nucleotides, or from 4 to 30 nucleotides, or from 8 to 20 nucleotides, respectively. In one aspect, oligonucleotide tags are used in sets, or repertoires, wherein each oligonucleotide tag of the set has a unique nucleotide sequence. In some embodiments, particularly where oligonucleotide tags are used to sort polynucleotides, or where they are identified by specific hybridization, each oligonucleotide tag of such a set has a melting temperature that is substantially the same as that of every other member of the same set. In such aspects, the melting temperatures of oligonucleotide tags within a set are within 10° C. of one another; in another embodiment, they are within 5° C. of one another; and in another embodiment, they are within 2° C. of one another. A set of oligonucleotide tags may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. Where oligonucleotide tags are used to label or identify fragments from a particular organism or species whose genome sequence is known, tag sequences may be selected to be distinguishable from the genomic sequences of such organism or species.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" are used interchangeably and each mean a linear polymer of nucleotide monomers. As used herein, the terms may also refer to double stranded forms. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like, to form duplex or triplex forms. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moities, or bases at any or some positions, when such analogs are incompatible with enzymatic reactions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 9 to 40 nucleotides, or in some embodiments, from 14 to 36 nucleotides.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Reference sequence" or "reference population" of DNA refers to individual DNA sequences or a collection of DNAs (or RNAs derived from it) which is compared to a test population of DNA or RNA, (or "test DNA sequence," or "test DNA population") by the formation of heteroduplexes between the complementary strands of the reference DNA population and test DNA population. If perfectly matched heteroduplexes form, then the respective members of the reference and test populations are identical; otherwise, they are variants of one another. Typically, the nucleotide sequences of members of the reference population are known and the sequences typically are listed in sequence databases, such as Genbank, Embl, or the like. In one aspect, a reference population of DNA may comprise a cDNA library or genomic library from a known cell type or tissue source. For example, a reference population of DNA may comprise a cDNA library or a genomic library derived from the tissue of a healthy individual and a test population of DNA may comprise a cDNA library or genomic library derived from the same tissue of a diseased individual. Reference populations of DNA may also comprise an assembled collection of individual polynucleotides, cDNAs, genes, or exons thereof, e.g. genes or exons encoding all or a subset of known p53 variants, genes of a signal transduction pathway, or the like.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature at which a population of double-stranded nucleic acid molecules becomes half dissociated into single strands. Several equations for calculating the Tm of nucleic acids are well known in the art. As indicated by standard references, a simple estimate of the Tm value may be calculated by the equation. $Tm=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" usually means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The above teachings are intended to illustrate the invention and do not by their details limit the scope of the claims of the invention. While preferred illustrative embodiments of the present invention are described, it will be apparent to one skilled in the art that various changes and modifications may be made therein without departing from the invention, and it is intended in the appended claims to cover all such changes and modifications that fall within the true spirit and scope of the invention.

The invention claimed is:

1. A method of preparing a tagged fragment library from a genome, comprising:
   a) providing a plurality of aliquots, at least some of which contain a plurality of first polynucleotides, wherein each first polynucleotide in an aliquot comprises a nucleotide sequence from a portion of the genome, and wherein, in at least sixty percent of the aliquots that contain first polynucleotides, the first polynucleotides do not comprise overlapping portions of the genome;
   b) replicating at least part of the nucleotide sequence of the first polynucleotides in at least some of the aliquots using tagged primers comprising a tag sequence, thereby producing tagged fragments in said aliquots, wherein the average fragment length of the tagged fragments in an aliquot is less than the length of the first polynucleotides in the aliquot, and wherein the tagged fragments in different aliquots are labeled with different tag sequences; and
   c) combining tagged fragments from the aliquots in step (b) together into a combined mixture, thereby producing the tagged fragment library,
   wherein the tagged primers in each aliquot comprise (i) a fragment binding portion that hybridizes to the first polynucleotide(s) in the aliquot and (ii) a tag portion that comprises the tag sequence.

2. The method of claim 1, further comprising obtaining sequence information from each of a plurality of the tagged fragments in the combined mixture,
   wherein the sequence information obtained from each tagged fragment includes genomic sequence and a tag sequence.

3. A method of preparing a tagged fragment library from a genome, comprising:
   a) providing a plurality of aliquots, at least some of which contain one or more first polynucleotides, wherein each first polynucleotide in an aliquot comprises a nucleotide sequence from a portion of the genome, and wherein, in at least sixty percent of the aliquots that contain first polynucleotides, the first polynucleotides do not comprise overlapping portions of the genome;
   b) replicating at least part of the nucleotide sequence of the first polynucleotides in at least some of the aliquots using tagged primers comprising a tag sequence, thereby producing tagged fragments in said aliquots, wherein the average fragment length of the tagged fragments in an aliquot is less than the length of the first polynucleotides in the aliquot, and wherein the tagged fragments in different aliquots are labeled with different tag sequences; and
   c) combining tagged fragments from the aliquots in step (h) together into a combined mixture, thereby producing the tagged fragment library,
   wherein the tagged primers in each aliquot comprise (i) a fragment binding portion that hybridizes to the genomic nucleotide sequence in the first polynucleotide (s) in the aliquot and (ii) a tag portion that comprises the tag sequence.

4. The method of claim 3, further comprising obtaining sequence information from each of a plurality of the tagged fragments in the combined mixture,
   wherein the sequence information obtained from each tagged fragment includes genomic sequence and a tag sequence.

5. A method of preparing a tagged fragment library from a genome, comprising:
  a) providing a plurality of aliquots, at least some of which contain one or more first polynucleotides, wherein each first polynucleotide in an aliquot comprises a nucleotide sequence from a portion of the genome,, and wherein, in at least sixty percent of the aliquots that contain first polynucleotides, the first polynucleotides do not comprise overlapping portions of the genome;
  b) replicating at least part of the nucleotide sequence of the first polynucleotides in at least some of the aliquots using tagged primers comprising a tag sequence, thereby producing tagged fragments in said aliquots, wherein the average fragment length of the tagged fragments in an aliquot is less than the length of the first polynucleotides in the aliquot, and wherein the tagged fragments in different aliquots are labeled with different tag sequences; and
  c) combining tagged fragments from the aliquots in step (b) together into a combined mixture, thereby producing the tagged fragment library,
  wherein the tagged primers in each aliquot comprise (i) a fragment binding portion that hybridizes to the first polynucleotide(s) in the aliquot and (ii) a tag portion that comprises the tag sequence,
  wherein the fragment binding portion of each tagged primer comprises a random sequence.

6. The method of claim 5, further comprising obtaining sequence information from each of a plurality of the tagged fragments in the combined mixture,
  wherein the sequence information obtained from each tagged fragment includes genomic sequence and a tag sequence.

7. The method of claim 1, wherein the fragment binding portion of each tagged primer in each aliquot comprises a random sequence.

8. The method of claim 3, wherein the fragment binding portion of each tagged primer in each aliquot comprises a random sequence.

9. The method of claim 7 or claim 8, wherein the random sequence is a sequence of 6 to 18 nucleotides.

10. The method of claim 1 or claim 5, wherein the fragment binding portions of the tagged primers in each aliquot hybridize to the genomic nucleotide sequence in the first polynucleotide(s) in the aliquot.

11. The method of claim 3 or claim 5, wherein at least some of the aliquots provided in step (a) contain a plurality of first polynucleotides.

12. The method of claim 1, claim 3, or claim 5, wherein in at least ninety percent of the aliquots the nucleotide sequence from any given portion of the genome is represented in only a single first polynucleotide in the aliquot.

13. The method of claim 1, claim 3, or claim 5, wherein the plurality of aliquots in (a) comprise at least 10 genome equivalents of DNA, and the number of aliquots in (a) is selected so that the probability of overlapping fragments in individual aliquots of the plurality is less than 0.1%.

14. The method of claim 1, claim 3, or claim 5, wherein the number of aliquots is at least 1536.

15. The method of claim 2, claim 4, or claim 6, wherein the step of obtaining the sequence information comprises:
  arraying the tagged fragments on a surface such that a majority of the fragments are optically resolvable;
  optionally amplifying the tagged fragments before or after the arraying; and
  obtaining sequence reads from the tagged fragments on the surface.

16. The method of claim 2, wherein the step of obtaining the sequence information includes sequencing by probe ligation.

17. The method of claim 2, claim 4, or claim 6, wherein the step of obtaining the sequence information includes sequencing by synthesis.

18. The method of claim 1, claim 3, or claim 5, wherein the genome is a mammalian genome.

* * * * *

UNITED STATES PATENT AND TRADEMARK OFFICE
CERTIFICATE OF CORRECTION

| | | |
|---|---|---|
| PATENT NO. | : 10,125,392 B2 | Page 1 of 1 |
| APPLICATION NO. | : 13/971797 | |
| DATED | : November 13, 2018 | |
| INVENTOR(S) | : Radoje Drmanac | |

It is certified that error appears in the above-identified patent and that said Letters Patent is hereby corrected as shown below:

In the Claims

In Column 45, Line 52:
In Claim 1, delete "polvnucleotides" and
Insert -- polynucleotides --.

In Column 45, Line 60:
In Claim 1, delete "tagportion" and
Insert -- tag portion --.

In Column 46, Line 55:
In Claim 3, delete "(h)" and
Insert -- (b) --.

In Column 47, Line 6:
In Claim 5, delete "genome,," and
Insert -- genome, --.

Signed and Sealed this
Twenty-eighth Day of March, 2023

Katherine Kelly Vidal
*Director of the United States Patent and Trademark Office*